(12) United States Patent
McCarthy et al.

(10) Patent No.: US 11,645,565 B2
(45) Date of Patent: May 9, 2023

(54) PREDICTIVE DATA ANALYSIS WITH CROSS-TEMPORAL PROBABILISTIC UPDATES

(71) Applicant: Optum Services (Ireland) Limited, Dublin (IE)

(72) Inventors: Michael J. McCarthy, Dublin (IE);
Kieran O'Donoghue, Dublin (IE);
Harutyun Shahumyan, Dublin (IE);
Neill Michael Byrne, Dublin (IE);
David Lewis Frankenfield, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 628 days.

(21) Appl. No.: 16/680,785

(22) Filed: Nov. 12, 2019

(65) Prior Publication Data

US 2021/0142199 A1     May 13, 2021

(51) Int. Cl.
 *G06N 7/00*     (2006.01)
 *G16H 50/20*    (2018.01)
 *G06N 20/20*    (2019.01)
 *G06N 20/00*    (2019.01)

(52) U.S. Cl.
 CPC .............. *G06N 7/005* (2013.01); *G06N 20/00* (2019.01); *G16H 50/20* (2018.01)

(58) Field of Classification Search
 CPC ........ G06N 7/005; G06N 20/00; G06N 5/003; G06N 3/0454; G06N 20/20; G16H 50/20; G16H 50/30; Y02A 90/10
 See application file for complete search history.

(56) References Cited

U.S. PATENT DOCUMENTS

| 6,110,109 A | 8/2000 | Hu et al. |
| 8,504,343 B2 | 8/2013 | Chawla et al. |
| 8,645,166 B2 | 2/2014 | Bessette |

(Continued)

FOREIGN PATENT DOCUMENTS

| CN | 107103364 A | * | 8/2017 | |
| CN | 107736890 A | * | 2/2018 | ............. A61B 5/112 |

(Continued)

OTHER PUBLICATIONS

Sina Sajadmanesh, "NP-GLM: A Non-Parametric Method for Temporal Link Prediction", 2017, Dept. of Computer Engineering, Sharif University of Technology, Tehran, Iran, pp. 1-7. (Year: 2017).*

(Continued)

*Primary Examiner* — Tan D Nguyen
(74) *Attorney, Agent, or Firm* — Alston & Bird LLP

(57) ABSTRACT

There is a need for solutions for more efficient predictive data analysis systems. This need can be addressed, for example, by a system configured to receive temporal inferences for a predictive task, where each temporal inference is associated with a temporal benchmark and the temporal benchmarks include a base temporal benchmark and supplemental temporal benchmarks; generate a cross-temporal prediction for the predictive task by applying one or more cross-temporal probabilistic updates to the base temporal inference, where each cross-temporal probabilistic update is associated with a supplemental temporal benchmark; and display the cross-temporal prediction using a cross-temporal prediction interface.

20 Claims, 14 Drawing Sheets

(56) References Cited

U.S. PATENT DOCUMENTS

| | | | |
|---|---|---|---|
| 9,858,390 | B2 | 1/2018 | Barhak |
| 10,468,142 | B1 | 11/2019 | Abou et al. |
| 2004/0083084 | A1 | 4/2004 | West |
| 2004/0225629 | A1 | 11/2004 | Eder |
| 2004/0260664 | A1 | 12/2004 | Thiesson et al. |
| 2008/0154821 | A1 | 6/2008 | Poulin |
| 2011/0004110 | A1 | 1/2011 | Shusterman |
| 2012/0179478 | A1 | 7/2012 | Ross |
| 2013/0085769 | A1 | 4/2013 | Jost et al. |
| 2014/0379310 | A1 | 12/2014 | Ramachandran et al. |
| 2016/0171383 | A1 | 6/2016 | Narain et al. |
| 2016/0360980 | A1 | 12/2016 | Sinha et al. |
| 2017/0049383 | A1 | 2/2017 | McMahon et al. |
| 2017/0300933 | A1 | 10/2017 | Mascaro et al. |
| 2017/0357879 | A1* | 12/2017 | Odaibo .......... G06N 3/0445 |
| 2018/0068224 | A1* | 3/2018 | Chen .......... G06N 5/02 |
| 2018/0285778 | A1 | 10/2018 | Nori et al. |
| 2018/0330824 | A1 | 11/2018 | Athey et al. |
| 2019/0005198 | A1 | 1/2019 | Richards et al. |
| 2019/0108912 | A1* | 4/2019 | Spurlock, III .......... G16H 50/20 |
| 2020/0351173 | A1* | 11/2020 | Vasseur .......... H04L 41/0681 |
| 2020/0387805 | A1 | 12/2020 | McCarthy et al. |

FOREIGN PATENT DOCUMENTS

| | | | | |
|---|---|---|---|---|
| WO | WO-2015057661 | A1 * | 4/2015 | .......... G10L 15/02 |
| WO | WO-2018132483 | A1 * | 7/2018 | |
| WO | 2020/247223 | A1 | 12/2020 | |

OTHER PUBLICATIONS

Divya Saxena, "D-GAN: Deep Generative Adversariel Nets for Spatio-Temporal Prediction", May 2019, 20XX IEEE, pp. 1-8. (Year: 2019).*

Yoon-Eui Nahm, "Integrated Product and Process Modeling for Collaborative Design Environment", Mar. 2004, Concurrent Engineering: Research and Applications, pp. 5-23. (Year: 2004).*

Umut Ozertem, "Learning to Suggest: A Machine Learning Framework for Ranking Query Suggestions", 2012, SIGIR's12, pp. 25-34. (Year: 2012).*

Srijan Kumar, "Predicting Dynamic Embedding Trajectory in Temporal Interaction Networks", KDD '19, Aug. 4-8, 2019, pp. 1269-1277. (Year: 2019).*

NonFinal Office Action for U.S. Appl. No. 16/432,535, dated Sep. 15, 2021, (59 pages), United States Patent and Trademark Office, USA.

Paranjape, Parnika N. et al., "Cross-Correlation Aided Ensemble of Classifiers for BCI Oriented EEG Study," IEEE Access, vol. 7, Jan. 2, 2019, Year: 2019, pp. 11985-11996, DOI: 10.1109/ACCESS.2019.2892492.

"Population Risk Management—To Change Your Population's Trajectory You Have to Know it," Ayasdi (9 pages), [online], [Retrieved From the Internet Sep. 4, 2019] <https://www.ayasdi.com/applications/population-health/>.

Bayati, Mohsen et al. "A Low-Cost Method for Multiple Disease Prediction," in AMIA Annual Symposium Proceedings, Nov. 5, 2015, vol. 2015, pp. 329-338. [Retrieved From the Internet Sep. 4, 2019] <https://www.ncbi.nlm.nih.gov/pmc/articles/PMC4765607/>.

Martinez-Beneito, Miguel A. et al. "Towards A Multidimensional Approach to Bayesian Disease Mapping," Bayesian Analysis, Mar. 12, 2017, vol. 12, No. 1, pp. 239-259. [Retrieved From the Internet Sep. 4, 2019 ] <https://projecteuclid.org/euclid.ba/1458324098>.

International Searching Authority, International Search Report and Written Opinion for International Application No. PCT/US2020/034773, Jul. 7, 2020, (11 pages), European Patent Office, Rijswijk, Netherlands.

Final Office Action for U.S. Appl. No. 16/432,535, dated Mar. 24, 2022, (46 pages), United States Patent and Trademark Office, USA.

NonFinal Office Action for U.S. Appl. No. 16/432,535, dated Jan. 4, 2023, (42 pages). United States Patent and Trademark Office, US.

Reps, Jenna M. et al. "Design and Implementation of a Standardized Framework to Generate and Evaluate Patient-Level Prediction Models Using Observational Healthcare Data," Journal of the American Medical Informatics Association AMIA, vol. 25, No. 8, Apr. 27, 2018, pp. 969-975, (Year: 2018), DOI: 10.1093/jamia/ocy032.

Rider, Andrew K. et al. "An Ensemble Topic Model for Sharing Healthcare Data and Predicting Disease Risk," in Proceedings of the International Conference on Bioinformatics, Computational Biology and Biomedical Informatics, ACM, Sep. 22-25, 2013, pp. 333-340, (Year: 2013).

* cited by examiner

PREDICTIVE DATA ANALYSIS WITH CROSS-TEMPORAL PROBABILISTIC UPDATES

BACKGROUND

Many existing conventional data analysis systems suffer from significant efficiency and utility drawbacks. Through ingenuity and innovation, various embodiments of the present invention make substantial improvements to the efficiency and reliability of predictive data analysis systems, including by addressing efficiency and utility drawbacks of those predictive data analysis systems.

BRIEF SUMMARY

In general, embodiments of the present invention provide methods, apparatus, systems, computing devices, computing entities, and/or the like for predictive data analysis with cross-temporal probabilistic updates. Certain embodiments utilize systems, methods, and computer program products that enable cross-temporal predictions generated based at least in part on cross-task predictions, where the cross-task predictions may in turn be generated based at least in part on cross-model predictions.

In accordance with one aspect, a method is provided. In one embodiment, the method includes receiving a plurality of temporal inferences for the predictive task, wherein: (i) each temporal inference is associated with a temporal benchmark of a plurality of temporal benchmarks, (ii) the plurality of temporal benchmarks comprises a base temporal benchmark and one or more supplemental temporal benchmarks, (iii) the base temporal benchmark is associated with a base temporal inference of the plurality of temporal inferences, and (iv) each supplemental temporal benchmark is associated with a corresponding supplemental temporal inference of one or more supplemental temporal inferences of the plurality of temporal inferences; generating the cross-temporal prediction for the predictive task by applying one or more cross-temporal probabilistic updates to the base temporal inference, wherein: (i) each cross-temporal probabilistic update is associated with a supplemental temporal benchmark of the one or more supplemental temporal benchmarks, and (ii) each cross-temporal probabilistic update is performed based at least in part on the supplemental temporal inference for a respective supplemental temporal benchmark of the one or more supplemental temporal benchmarks associated with the cross-temporal probabilistic update; and providing the cross-temporal prediction for display using a cross-temporal prediction interface.

In accordance with another aspect, a computer program product is provided. The computer program product may comprise at least one computer-readable storage medium having computer-readable program code portions stored therein, the computer-readable program code portions comprising executable portions configured to receive a plurality of temporal inferences for the predictive task, wherein: (i) each temporal inference is associated with a temporal benchmark of a plurality of temporal benchmarks, (ii) the plurality of temporal benchmarks comprises a base temporal benchmark and one or more supplemental temporal benchmarks, (iii) the base temporal benchmark is associated with a base temporal inference of the plurality of temporal inferences, and (iv) each supplemental temporal benchmark is associated with a corresponding supplemental temporal inference of one or more supplemental temporal inferences of the plurality of temporal inferences; generate the cross-temporal prediction for the predictive task by applying one or more cross-temporal probabilistic updates to the base temporal inference, wherein: (i) each cross-temporal probabilistic update is associated with a supplemental temporal benchmark of the one or more supplemental temporal benchmarks, and (ii) each cross-temporal probabilistic update is performed based at least in part on the supplemental temporal inference for a respective supplemental temporal benchmark of the one or more supplemental temporal benchmarks associated with the cross-temporal probabilistic update; and provide the cross-temporal prediction for display using a cross-temporal prediction interface.

In accordance with yet another aspect, an apparatus comprising at least one processor and at least one memory including computer program code is provided. In one embodiment, the at least one memory and the computer program code may be configured to, with the processor, cause the apparatus to receive a plurality of temporal inferences for the predictive task, wherein: (i) each temporal inference is associated with a temporal benchmark of a plurality of temporal benchmarks, (ii) the plurality of temporal benchmarks comprises a base temporal benchmark and one or more supplemental temporal benchmarks, (iii) the base temporal benchmark is associated with a base temporal inference of the plurality of temporal inferences, and (iv) each supplemental temporal benchmark is associated with a corresponding supplemental temporal inference of one or more supplemental temporal inferences of the plurality of temporal inferences; generate the cross-temporal prediction for the predictive task by applying one or more cross-temporal probabilistic updates to the base temporal inference, wherein: (i) each cross-temporal probabilistic update is associated with a supplemental temporal benchmark of the one or more supplemental temporal benchmarks, and (ii) each cross-temporal probabilistic update is performed based at least in part on the supplemental temporal inference for a respective supplemental temporal benchmark of the one or more supplemental temporal benchmarks associated with the cross-temporal probabilistic update; and provide the cross-temporal prediction for display using a cross-temporal prediction interface.

BRIEF DESCRIPTION OF THE DRAWINGS

Figure 1:
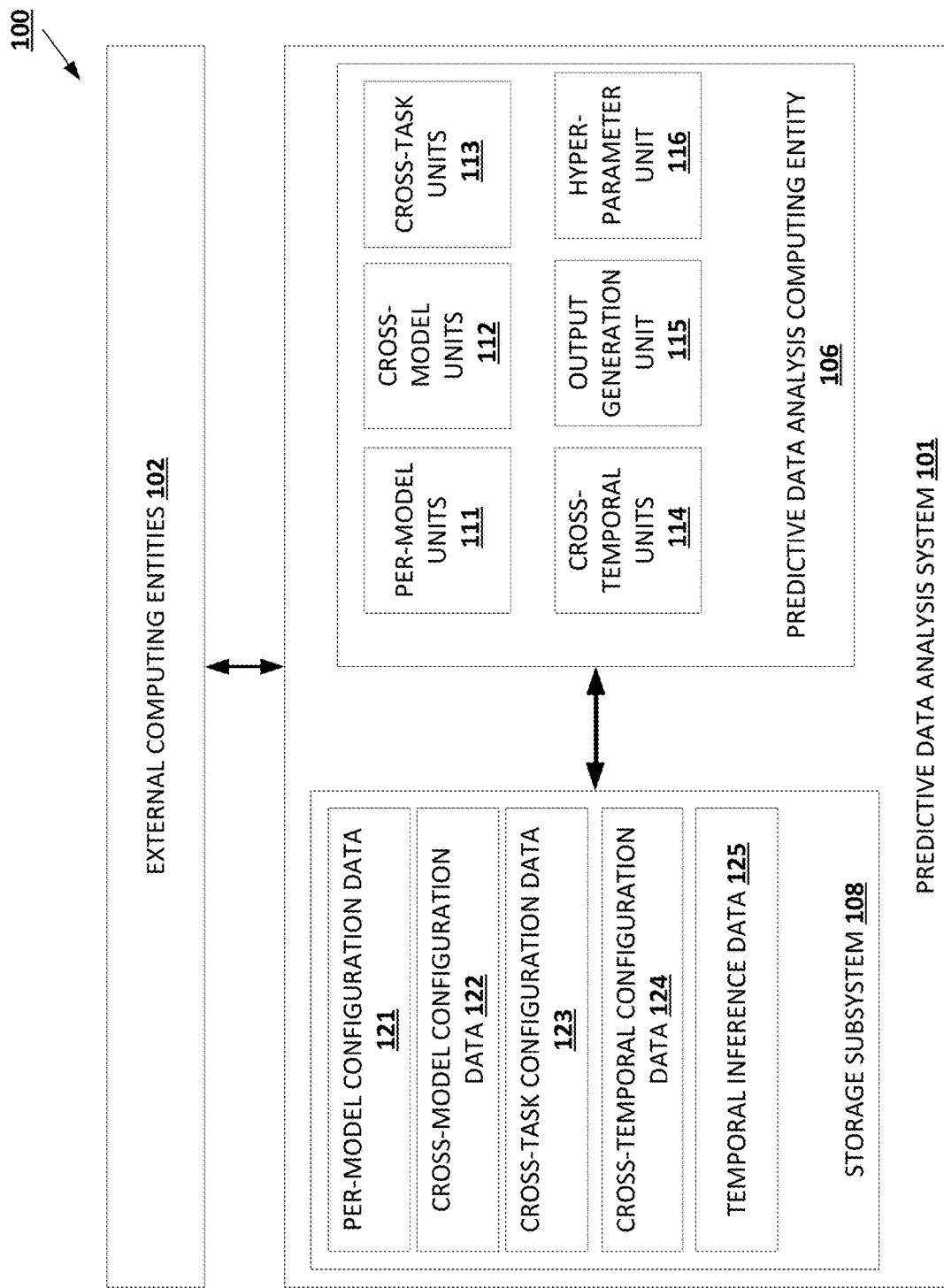

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
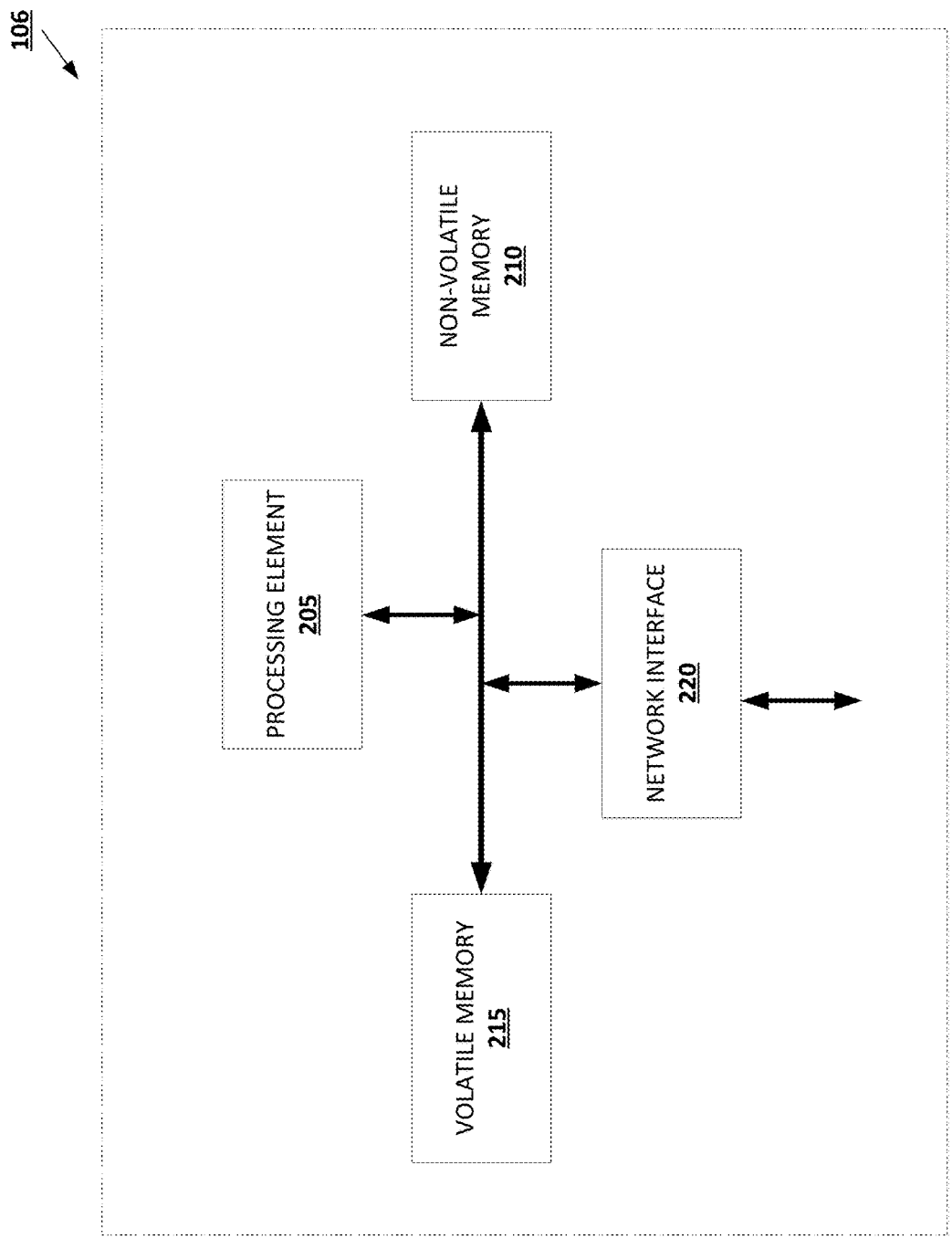

FIG. 2 provides an example predictive data analysis computing entity in accordance with some embodiments discussed herein.

Figure 3:
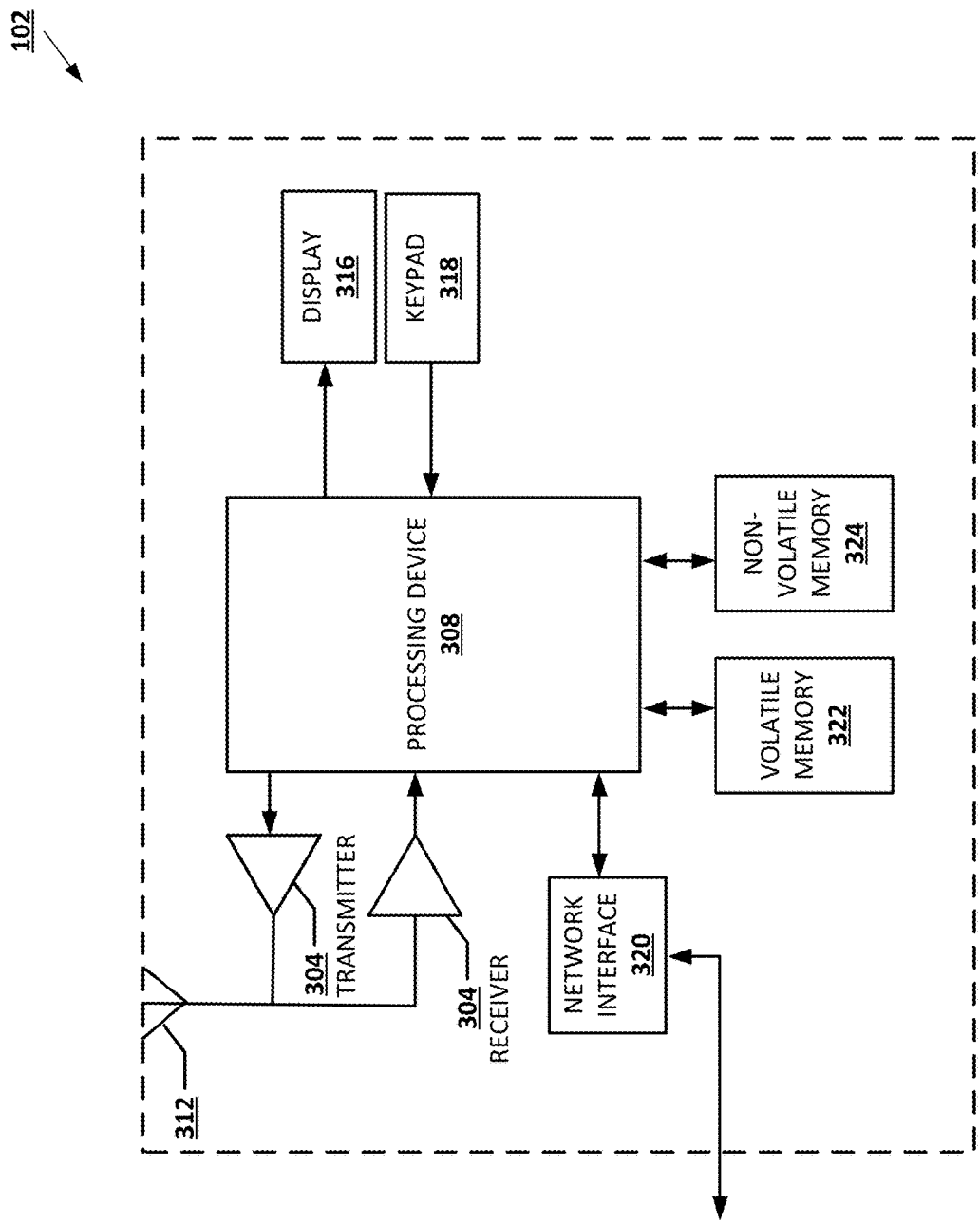

FIG. 3 provides an example external computing entity in accordance with some embodiments discussed herein.

Figure 4:
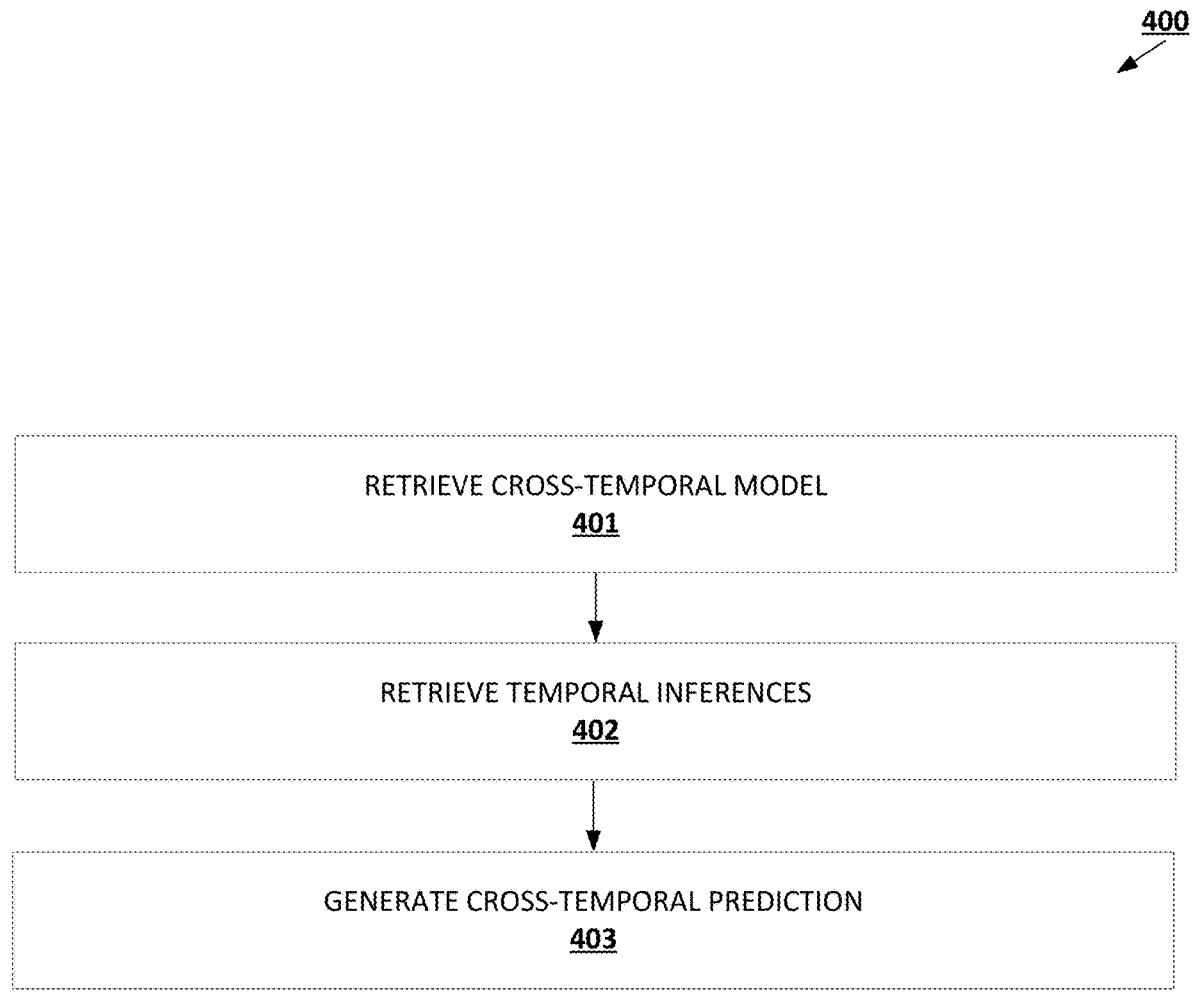

FIG. 4 is a flowchart diagram of an example process for generating a cross-temporal prediction for a predictive task in accordance with some embodiments discussed herein.

Figure 5:
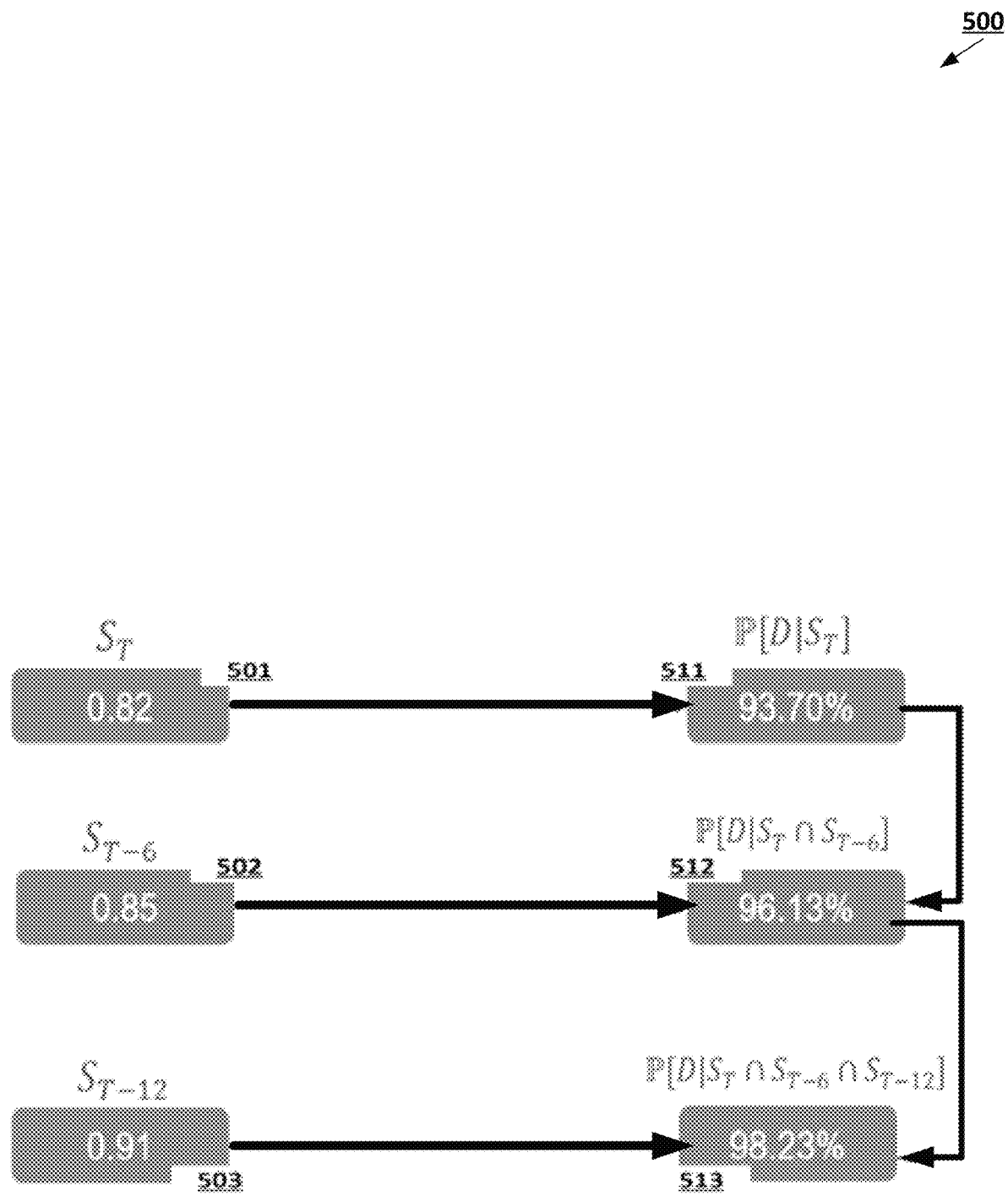

FIG. 5 provides an operational example of a cross-temporal prediction generation order in accordance with some embodiments discussed herein.

Figure 6:
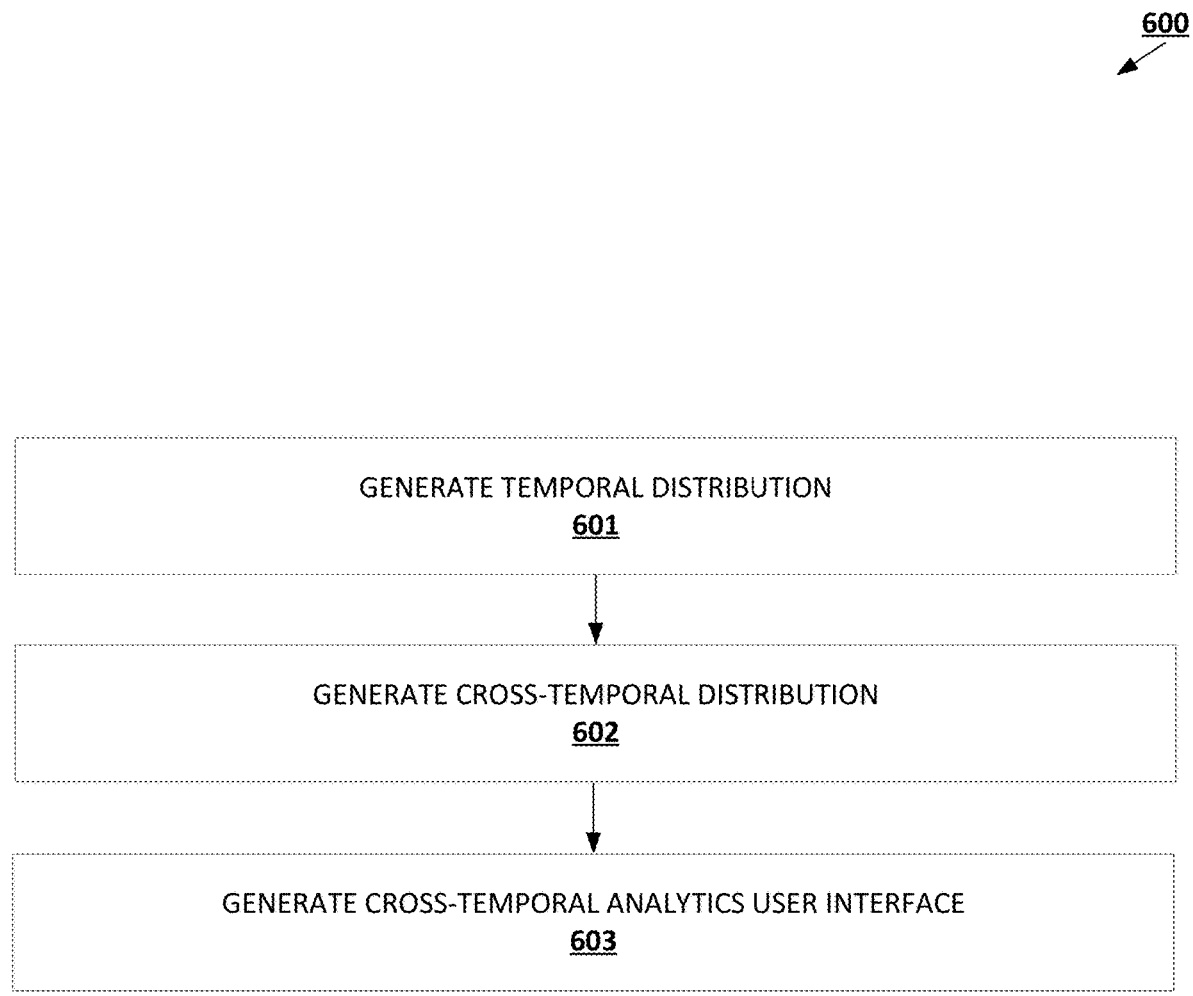

FIG. 6 is a flowchart diagram of an example process for generating a cross-temporal analytics user interface for a predictive task in accordance with some embodiments discussed herein.

Figure 7:
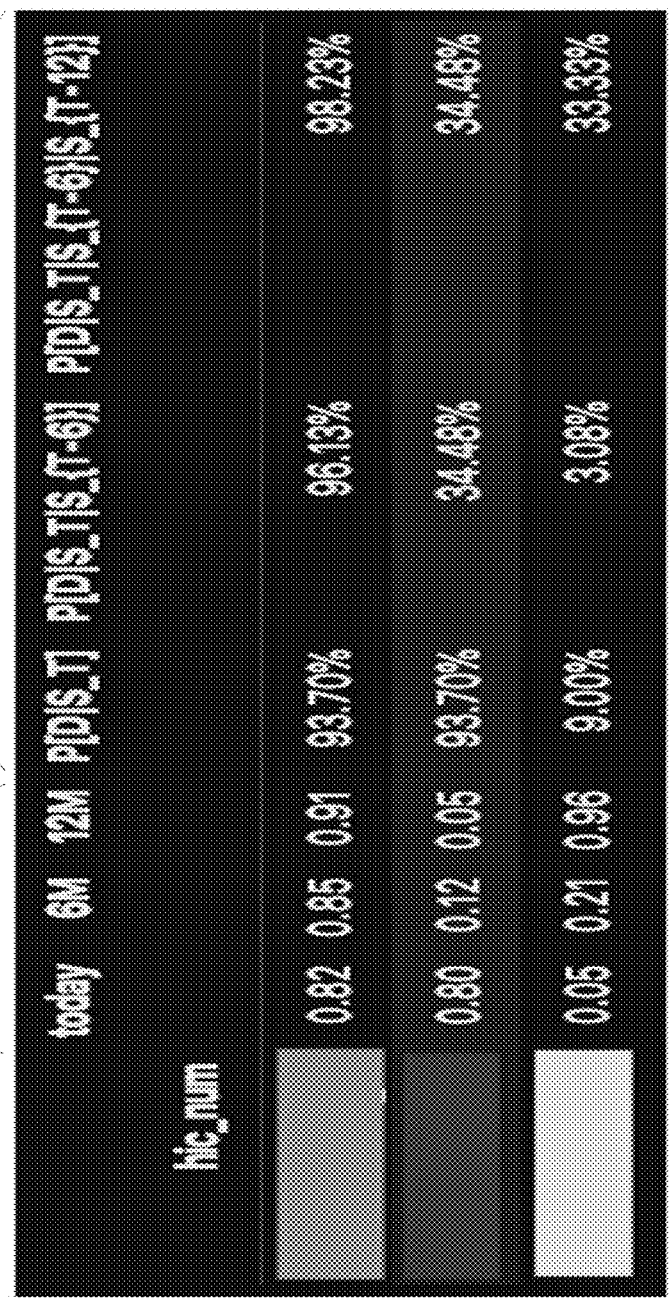

FIG. 7 provides an operational example of a cross-temporal analytics user interface for a predictive task in accordance with some embodiments discussed herein.

Figure 8:
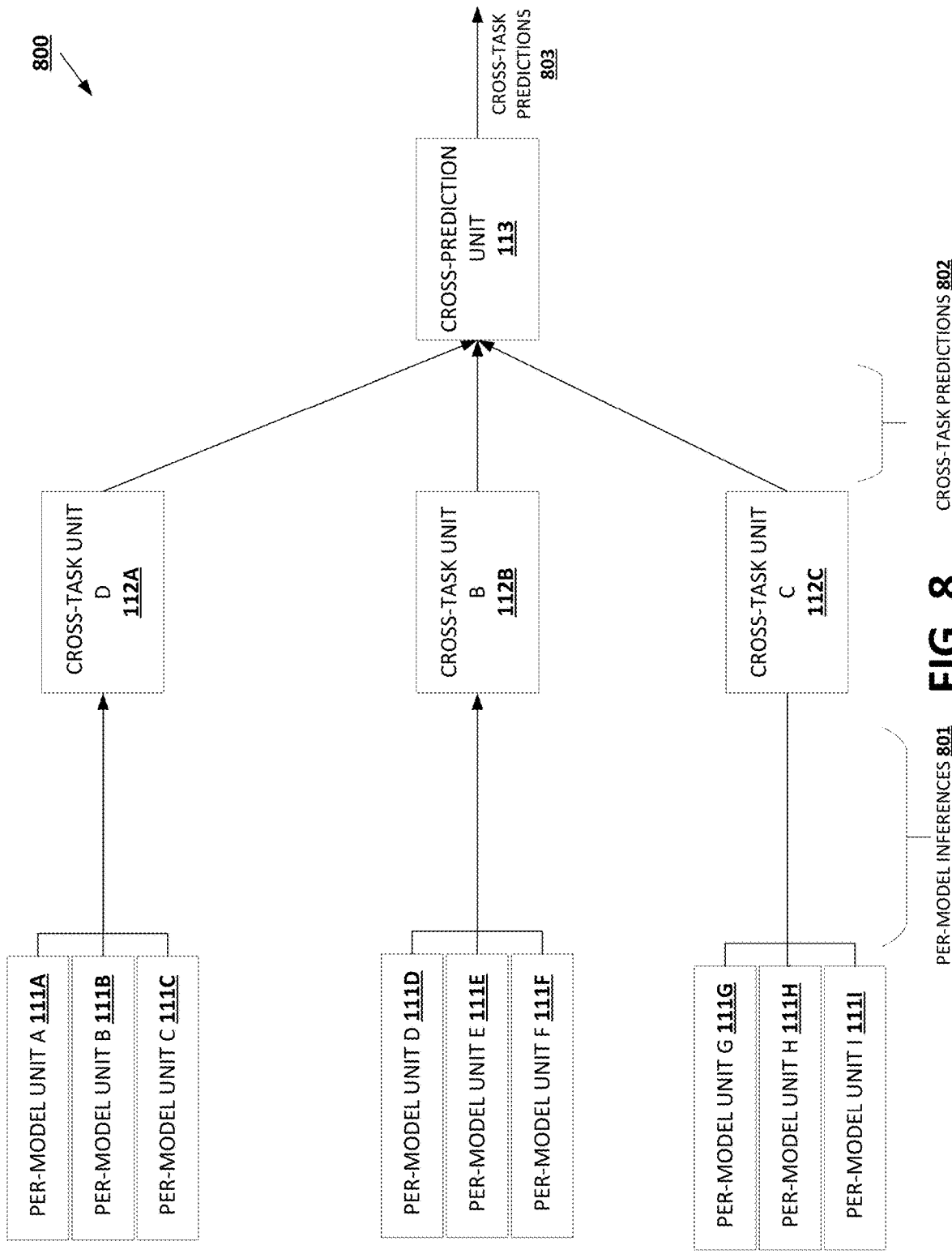

FIG. 8 is a data flow diagram of an example process for generating cross-task predictions in accordance with some embodiments discussed herein.

Figure 9:
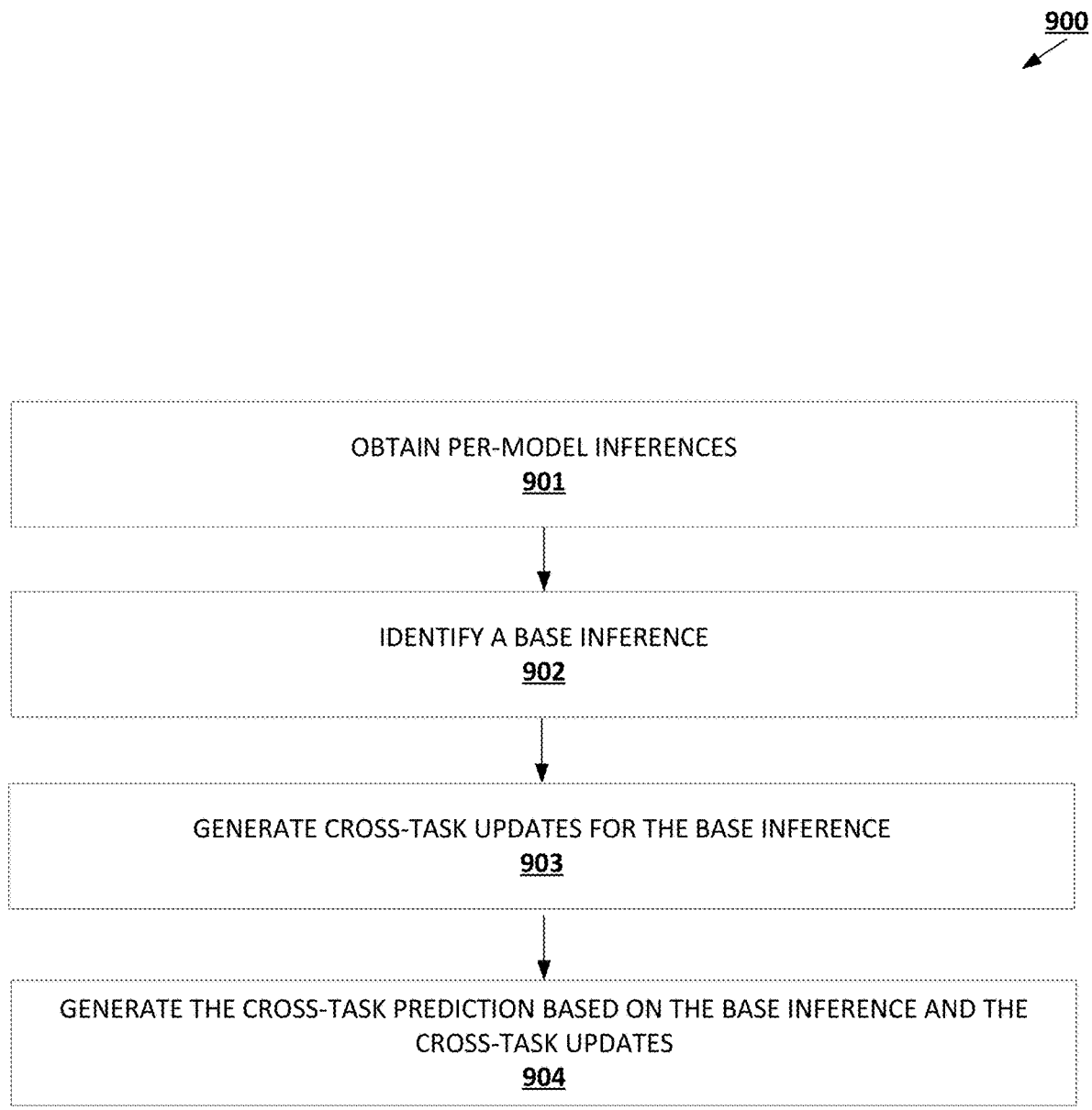

FIG. 9 is a flowchart diagram of an example process for generating a cross-model prediction in accordance with some embodiments discussed herein.

Figure 10:
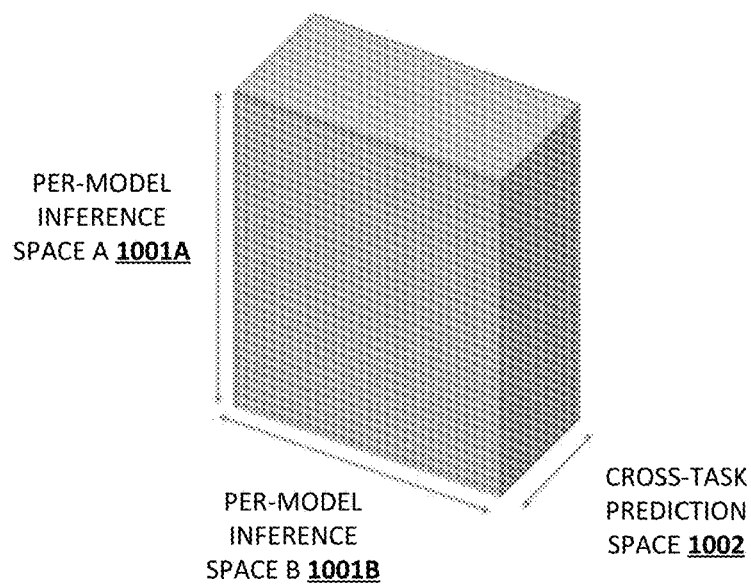

FIG. 10 provides an operational example of a cross-model distribution in accordance with some embodiments discussed herein.

Figure 11:
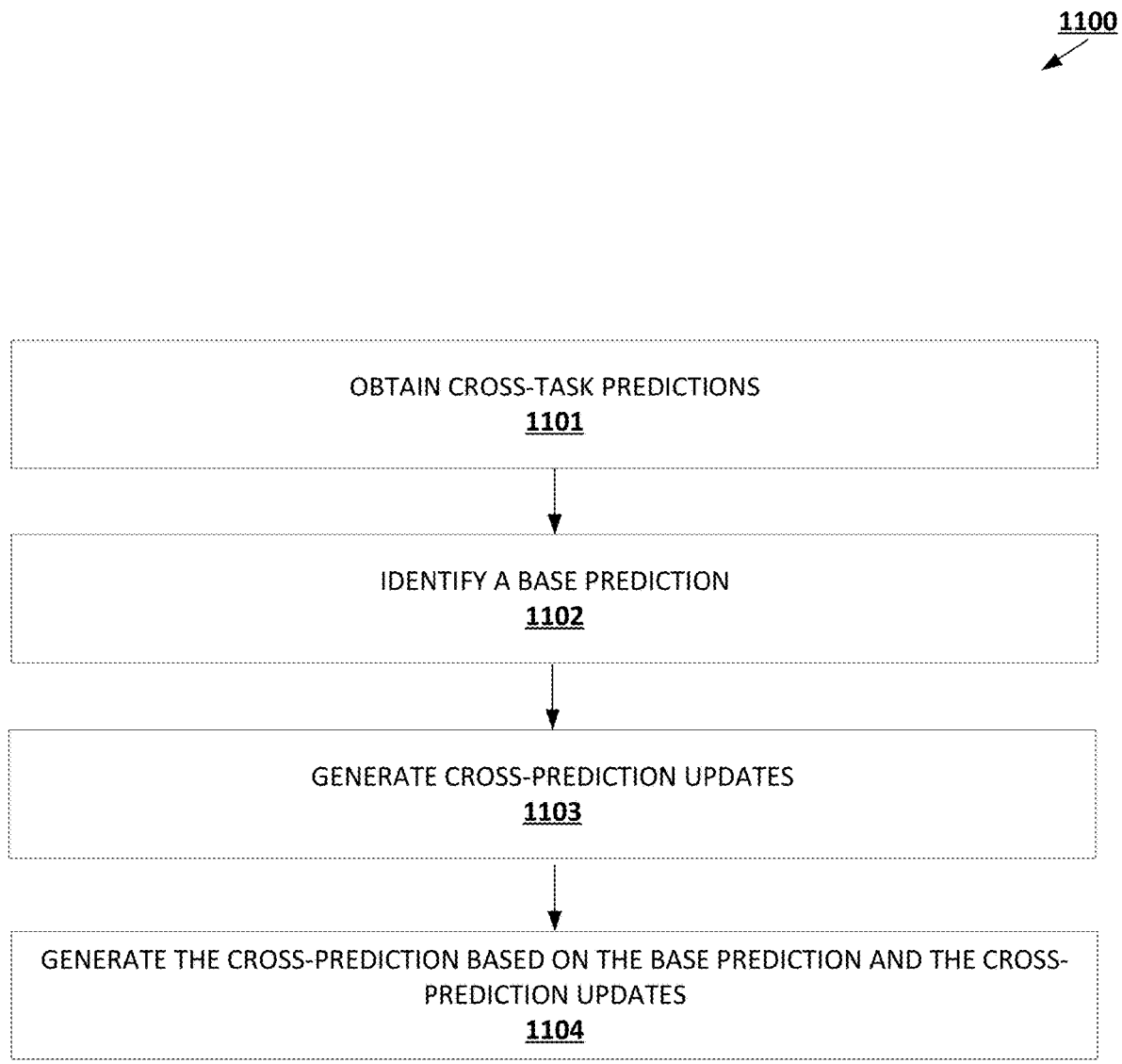

FIG. 11 is a flowchart diagram of an example process for generating a cross-task prediction in accordance with some embodiments discussed herein.

Figure 12:
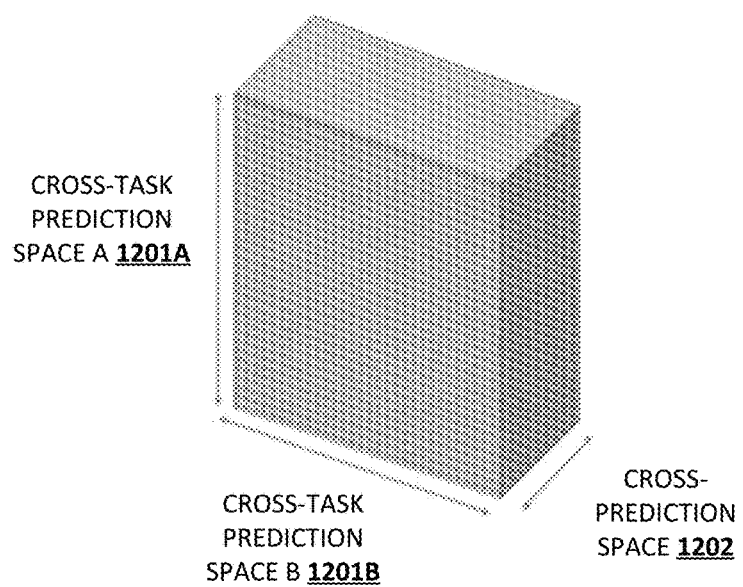

FIG. 12 provides an operational example of a cross-task prediction distribution in accordance with some embodiments discussed herein.

Figure 13:
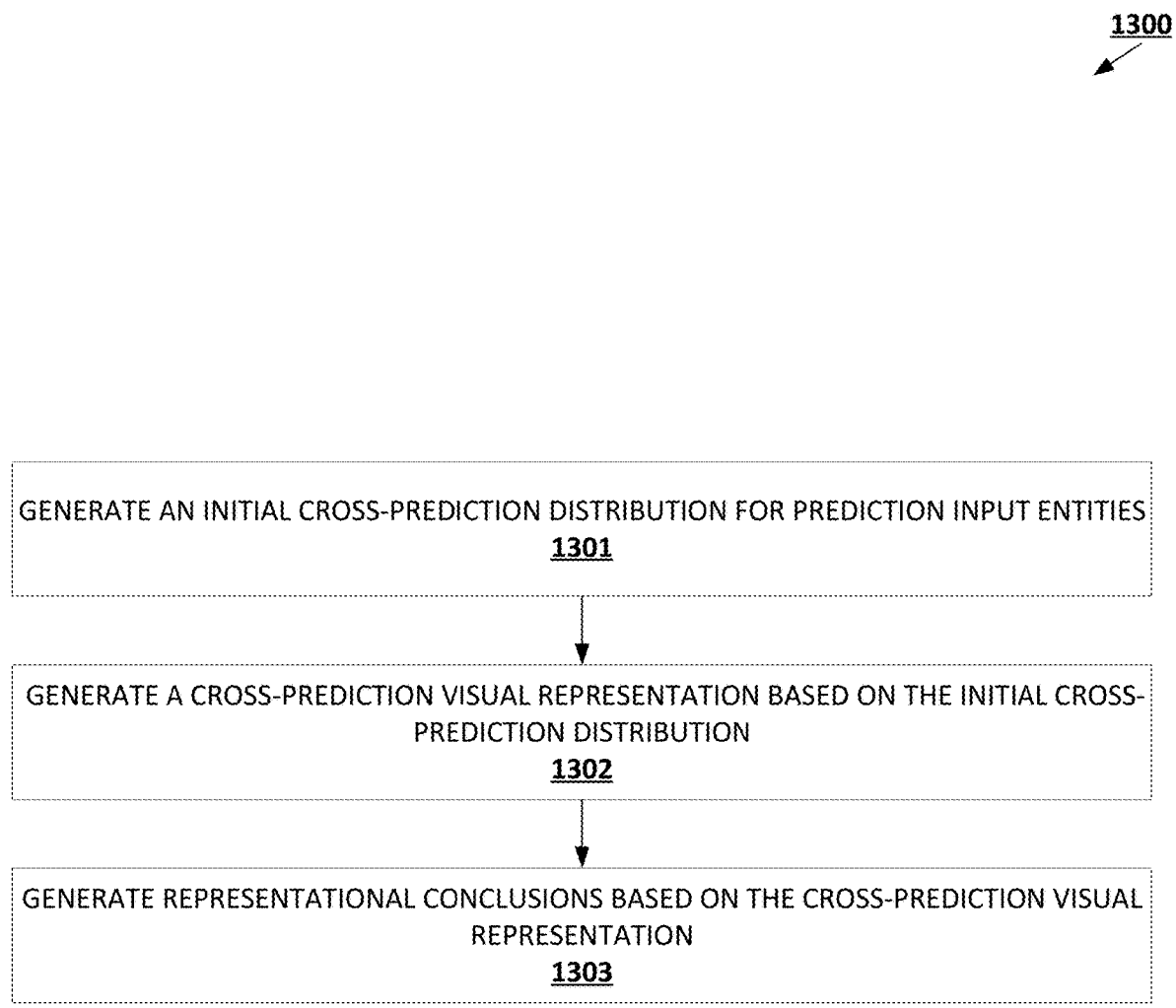

FIG. 13 is a flowchart diagram of an example process for generating representational conclusions accordance with some embodiments discussed herein.

Figure 14:
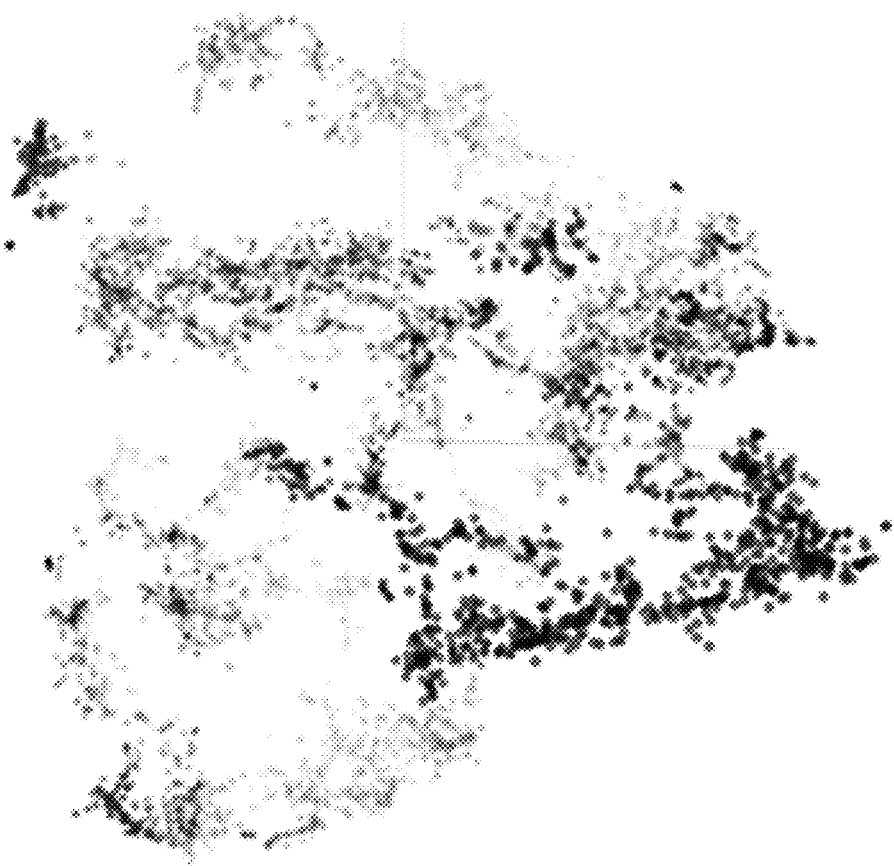

FIG. 14 provides an operational example of a cross-task prediction visual representation in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also may include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also may include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also may include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an exemplary overview of an architecture 100 that can be used to practice embodiments of the present invention. The architecture 100 includes a predictive data analysis system 101 and one or more external computing entities 102. In some embodiments, the external computing entities 102 provide prediction inputs to the predictive data analysis system 101. The predictive data analysis system 101 is configured to generate predictive data analysis outputs based at least in part on the received prediction inputs and provide the generated predictive data analysis outputs to the external computing entities 102. For example, the external computing entities 102 may provide patient data to the predictive data analysis system 101, while the predictive data analysis system 101 may generate multi-morbidity cross-temporal predictions based at least in part on the patient data and provide the generated multi-morbidity cross-temporal predictions to the external computing entities 102.

In some embodiments, the predictive data analysis system 101 interacts with the one or more external computing entities 102 over a communication network (not shown). The communication network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 includes a predictive data analysis computing entity 106 and a storage subsystem 108. The predictive data analysis computing entity 106 may be configured to generate cross-temporal predictions based at least in part on prediction inputs by using configuration data stored in the storage subsystem 108. The predictive data analysis computing entity 106 may further be configured to generate cross-temporal analytical user interfaces that contain cross-temporal visual representations based at least in part on the generated cross-temporal predictions and cause the external computing entities 102 to render the cross-temporal analytical user interfaces. The storage subsystem 108 may be configured to store configuration data utilized by the predictive data analysis computing entity 106 to generate cross-temporal predictions. The storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

The predictive data analysis computing entity 106 includes one or more per-model units 111 each associated with a corresponding predictive model and a corresponding predictive task; one or more cross-model units 112 each associated with a corresponding predictive task; one or more cross-task units 113 each associated with a corresponding predictive task; one or more cross-temporal units 114 each associated with a corresponding predictive task; an output generation unit 115, and a hyper-parameter unit 116. The storage subsystem 108 stores per-model configuration data 121, cross-model configuration data 122, cross-task configuration data 123, cross-temporal configuration data 124, and temporal inference data 125. Aspects of the various functionalities and/or stored contents of the mentioned components of the predictive data analysis computing entity 106 and the storage subsystem 108 are described in greater detail below.

Each per-model unit 111 may be configured to apply a corresponding predictive model to one or more most recent prediction inputs associated with a corresponding predictive task to generate a per-model inference associated with the corresponding predictive task and the corresponding predictive model. For example, an example per-model unit 111 may be associated with a bidirectional neural network predictive model and a corresponding predictive task related to diabetes risk prediction for a first patient profile. In the noted example, the mentioned example per-model unit 111 may process the most recent prediction inputs associated with the corresponding predictive task in accordance with the per-model configuration data 121 for the bidirectional neural network predictive model to generate a corresponding per-model prediction that describes a diabetes risk prediction for a first patient profile which has been determined using the bidirectional neural network predictive model. Each per-model unit 111 associated with a corresponding predictive task may then provide the generated per-model prediction to a cross-model unit 112 associated with the corresponding predictive task.

Each cross-model unit 112 may be configured to combine per-model inferences for a corresponding predictive task in accordance with a cross-model ensemble model for the corresponding predictive task to generate a cross-model prediction for the corresponding predictive task, where the cross-model ensemble model for the corresponding predictive task may be defined by the cross-model configuration data 122 for the corresponding predictive task. For example, a cross-model unit 112 associated with a corresponding per-model predictive task related to determining a diabetes risk prediction for a first patient profile may combine a per-model inference for the corresponding predictive task generated in accordance with a bidirectional neural network predictive model and a per-model inference for the corresponding predictive task generated in accordance with a Bayesian network predictive model to generate a cross-model prediction for the corresponding predictive task. Each cross-model unit 112 associated with a corresponding predictive task may then provide the generated cross-model prediction for the corresponding predictive task to a cross-task unit 113 associated with the corresponding predictive task.

Each cross-task unit 113 may be configured to process cross-model predictions for multiple predictive tasks (e.g., multiple related predictive tasks) in accordance with a cross-task ensemble model for a corresponding predictive task of the multiple predictive tasks to generate a cross-task prediction for the corresponding predictive task, where the cross-task ensemble model for the corresponding predictive task may be defined by the cross-task configuration data 123. For example, a cross-task unit 113 associated with a corresponding predictive task related to determining a diabetes risk prediction for a first patient profile may process the cross-model prediction for the corresponding predictive task in accordance with the cross-model prediction for another predictive task related to determining an HIV risk prediction for the first patient profile to generate a cross-task prediction for the corresponding predictive task. Each cross-task unit 113 associated with a corresponding predictive task may then store the generated cross-task prediction for the corresponding predictive task as part of the temporal inference data 125.

A cross-temporal unit 114 associated with a corresponding predictive task may be configured to retrieve cross-task predictions for the corresponding predictive task across a plurality of temporal benchmarks from the temporal inference data 125 and process the retrieved cross-task predictions for the corresponding predictive task in accordance with a cross-temporal ensemble model for the corresponding predictive task to generate a cross-temporal prediction for the corresponding predictive task, wherein the cross-temporal ensemble model for the corresponding predictive task may be defined based at least in part on the cross-temporal configuration data 124. For example, a cross-temporal unit 114 associated with a corresponding predictive task related to determining a diabetes risk prediction for a first patient profile may process a first cross-task prediction for the corresponding predictive task determined using current data, a second cross-task prediction for the corresponding predictive task determined using six-months-old data, and a third cross-task prediction for the corresponding predictive task determined using twelve-months-old data to generate a cross-temporal prediction for the corresponding predictive task. Each cross-temporal unit 114 may then provide the generated cross-temporal prediction to the output generation unit 115.

The output generation unit 115 may be configured to generate data analysis outputs based at least in part on at least one of one or more per-model inferences, one or more cross-model predictions, one or more cross-task predictions, and one or more cross-temporal predictions. The output generation unit 115 may further be configured to provide the generated data analysis outputs to at least some of the external computing entities 102. The output generation unit 115 may further be configured to generate analytical user interfaces such as cross-task analytical user interfaces and cross-temporal analytics and provide the generated analytical user interfaces to at least some of the external computing entities 102.

The hyper-parameter unit 116 may be configured to generate hyper-parameters for at least one of one or more predictive models defined by the per-model configuration data 121, one or more cross-model ensemble models defined by the cross-model configuration data 122, one or more cross-task ensemble models defined by the cross-task configuration data 123, and one or more cross-temporal ensemble models defined by the cross-temporal configuration data 124. For example, the hyper-parameter unit 116 may define a tuned supplemental temporal benchmark count hyper-parameter that defines the number of supplemental temporal benchmarks utilized to generate a particular cross-temporal prediction for a corresponding predictive task. As another example, the hyper-parameter unit 116 may define a tuned benchmark identity hyper-parameter that defines the timestamp and/or time interval for each of at least one particular supplemental temporal benchmark utilized to generate a particular cross-temporal prediction for a corresponding predictive task. As a further example, the hyper-parameter unit 116 may define a tuned benchmark order hyper-parameter that defines a cross-temporal order associated with the supplemental temporal benchmarks utilized to generate a particular cross-temporal prediction for a corresponding predictive task.

Exemplary Predictive Data Analysis Computing Entity

FIG. 2 provides a schematic of a predictive data analysis-computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also may include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further may include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further may include or be in communication with volatile media (also referred to as volatile storage, memory, memory storage, memory circuitry and/or similar terms used herein interchangeably). In one embodiment, the volatile storage or memory may also may include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also may include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1x (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis-computing entity 106 may also may include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can may include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MIMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can may include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can may include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also may include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

III. OVERVIEW

Discussed herein methods, apparatus, systems, computing devices, computing entities, and/or the like for predictive data analysis with probabilistic updates. As will be recognized, however, the disclosed concepts can be used to perform other types of data analysis.

Technical Problems

Various conventional predictive data analysis systems suffer from significant efficiency and accuracy drawbacks resulting from multiplicity of predictive inferences performed over various time intervals. For example, various existing predictive data analysis solutions fail to offer efficient and effective mechanisms for integrating predictive inferences performed over various time intervals. In some cases, existing predictive data analysis solutions either fail to integrate historical predictions in adjusting current predictions or perform such temporal integrations in a naïve and often computationally expensive manner. This problem is confounded in predictive models that, due to the complexity of their applicable predictive domains, resort to utilizing multiple predictive models and integrating hyper-parameters configured to address structural complexities of predictive tasks. In such instances, each temporal inference performed at a time may be both costly and with limited utility absent cross-temporal considerations. Thus, to address the significant efficiency and accuracy drawbacks resulting from multiplicity of predictive inferences performed over various time intervals, there is a technical need for predictive data analysis systems that perform reliable and efficient cross-temporal inferences.

Moreover, various conventional predictive data analysis systems suffer from efficiency and accuracy drawbacks resulting from multiplicity of predictive models as well as structural complexity of predictive tasks. Complex predictive input spaces are characterized by various desired predictive outputs that can each be estimated using a variety of available predictive models. This input space complexity creates considerable efficiency challenges for conventional predictive data analysis systems. Naïve approaches to addressing the noted predictive model duplicity challenges and the noted predictive task complexity challenges may lead to cross-model predictive solutions that are both computationally and storage-wise inefficient. To address such efficiency challenges, there is a technical need for predictive data analysis solutions that properly address challenges associated with managing predictive model duplicity and predictive task complexity challenges of predictive data analysis systems integrated with complex predictive input spaces.

Technical Solutions

Various embodiments of the present invention address technical challenges related to efficiency of predictive data analysis systems by using cross-temporal prediction solutions that integrate historical predictions using cross-temporal probabilistic updates, such as cross-temporal Bayesian updates. By doing so, various embodiments of the present invention provide efficient and effective means for integrating historical predictions in adjusting current predictions. For example, given two predictive tasks with identical current predictions but with distinct historical predictions where the historical prediction for a first predictive task confirms the current prediction for the first predictive task while the historical prediction for a second predictive task does not confirm the current prediction for the second predictive task, the confirmatory nature of the historical prediction for the first predictive task may be used to boost the significance of the current prediction for the first predictive task while the non-confirmatory nature of the historical prediction for the second predictive task may be used to discount the significance of the current prediction for the second predictive task. The noted adjustments of current predictions using historical predictions can be performed using efficient and reliable probabilistic updates, where update factors utilized to modify current predictions based at least in part on historical predictions. Through utilizing the noted adjustments, various embodiments of the present invention address technical challenges related to significant efficiency and accuracy drawbacks resulting from multiplicity of predictive inferences performed over various time intervals and make important technical contributions to improving efficiency and accuracy of predictive data analysis system.

Moreover, various embodiments of the present invention address technical challenges related to efficiency of predictive data analysis systems by using cross-predictive-task inference techniques that utilize cross-task probabilistic updates. In some embodiments, multiple per-model inferences generated by applying a predictive model in relation to a predictive task are aggregated in accordance with a cross-model ensemble model to generate a cross-model prediction for the predictive task. In some of those embodiments, various cross-model predictions for various predictive tasks are then aggregated to generate cross-task predictions for predictive tasks. Such an arrangement of per-model units, cross-model units, and cross-task predictions provides efficient techniques for addressing predictive model duplicity and predictive task complexity challenges of complex predictive input spaces. In this way, various embodiments of the present invention address efficiency drawbacks resulting from failure of conventional predictive data analysis systems to respond to challenges associated with multiplicity of predictive models as well as structural complexity of predictive tasks.

Definitions of Certain Terms

The term "predictive task" refers to determining a likelihood of occurrence of one or more conditions, such as one or more real-world entities and/or one or more real-world properties, with respect to particular prediction inputs. Examples of predictive tasks include cancer prediction for patients and based at least in part on patient data, Alzheimer's disease prediction for patients and based at least in part on patient data, Crohn's disease prediction for patients and based at least in part on patient data, prediction of cancer-plus-Alzheimer's-disease for patients and based at least in part on patient data, prediction of cancer-minus-Alzheimer's-disease for patients and based at least in part on patient data, etc.

The term "per-model inference" for a predictive task refers to data generated by applying a predictive model to a predictive input for the predictive task, where the data indicates a value for the likelihood of occurrence characterizing the predictive task. For example, a particular per-model inference may be generated by applying a neural network predictive model to a predictive input for a cancer prediction predictive task.

The term "cross-model prediction" for a predictive task refers to data generated by combining one or more per-model inferences associated with a predictive task, where the data indicate a value for the likelihood of occurrence characterizing the predictive task. For example, a particular cross-model prediction for a cancer prediction predictive task may be generated by combining the following per-model inferences: a per-model inference for the cancer prediction predictive task generated based at least in part on a neural network predictive model, a per-model inference for the cancer prediction predictive task generated based at least in part on a Bayesian network predictive model, and a per-model inference for the cancer prediction predictive task generated based at least in part on a decision tree predictive model. A cross-model prediction for a predictive task may be determined based at least in part on a cross-model ensemble model for the predictive task.

The term "cross-model ensemble model" refers to data describing operations and/or parameters utilized to combine one or more per-model inferences to generate a cross-model prediction. For example, in accordance with a particular cross-model ensemble model, each per-model inference of one or more per-model inferences is transformed in accordance with a cross-model ensemble parameter to generate a transformed per-model inference and the transformed per-model inferences are then combined to generate a cross-model prediction.

The term "cross-task prediction" for a particular predictive task refers to data generated by combining two or more predictions (e.g., including one or more cross-model predictions), where the two or more predictions include a prediction for the particular predictive task and one or more related predictions each associated with a predictive task other than the particular predictive task. For example, a cross-task prediction for a cancer predictive task may indicate a prediction about a likelihood of occurrence of cancer in a patient given a likelihood of occurrence of Alzheimer's disease. As another example, a cross-task prediction for a cancer-plus-Crohn's-disease predictive task may indicate a prediction about a likelihood of occurrence of cancer in a patient given a likelihood of occurrence of Alzheimer's disease in the patient. As a further example, a cross-task prediction for a cancer predictive task may indicate a prediction about a likelihood of occurrence of cancer in a patient given a per-model inference associated with occurrence of cancer in the patient based at least in part on a predictive model and a cross-model prediction associated with occurrence of Alzheimer's disease in the patient.

The term "cross-temporal prediction" for a particular predictive task refers to data generated by combining two or more predictions (e.g., including one or more cross-model predictions and/or one or more cross-task predictions) for the particular predictive task, where each of the two or more predictions is generated based at least in part on data associated with a temporal benchmark. For example, a cross-temporal prediction for a corresponding predictive task may be determined based at least in part on a first cross-task prediction for the corresponding predictive task determined using current data, a second cross-task prediction for the corresponding predictive task determined using six-months-old data, and a third cross-task prediction for the corresponding predictive task determined using twelve-months-old data to generate a cross-temporal prediction for the corresponding predictive task.

The term "temporal benchmark" refers to data that defines a point in time and/or an interval of time, where the point in time and/or the interval of time may be associated with prediction input data available as of time the point in time and/or the interval of time. Examples of temporal benchmarks include a temporal benchmark associated with a current time (i.e., a prediction time), a temporal benchmark associated with a historical time (e.g., six months ago), etc. In some embodiments, at least one of the temporal benchmarks used to generate cross-temporal predictions for a corresponding predictive task are determined by one or more training algorithms.

IV. EXEMPLARY SYSTEM OPERATION

Various embodiments of the present invention address technical challenges related to efficiency of predictive data analysis systems by using cross-temporal prediction solutions that integrate historical predictions using cross-temporal probabilistic updates, such as cross-temporal Bayesian updates. By doing so, various embodiments of the present invention provide efficient and effective means for integrating historical predictions in adjusting current predictions. For example, given two predictive tasks with identical current predictions but with distinct historical predictions where the historical prediction for a first predictive task confirms the current prediction for the first predictive task while the historical prediction for a second predictive task does not confirm the current prediction for the second predictive task, the confirmatory nature of the historical prediction for the first predictive task may be used to boost the significance of the current prediction for the first predictive task while the non-confirmatory nature of the historical prediction for the second predictive task may be used to discount the significance of the current prediction for the second predictive task. The noted adjustments of current predictions using historical predictions can be performed using efficient and reliable probabilistic updates, where update factors utilized to modify current predictions based at least in part on historical predictions. Through utilizing the noted adjustments, various embodiments of the present invention address technical challenges related to significant efficiency and accuracy drawbacks resulting from multiplicity of predictive inferences performed over various time intervals and make important technical contributions to improving efficiency and accuracy of predictive data analysis systems.

Various embodiments of the present invention address technical challenges related to efficiency of predictive data analysis systems by using cross-predictive-task inference techniques that utilize cross-task probabilistic updates. In some embodiments, multiple per-model inferences generated by applying a predictive model in relation to a predictive task are aggregated in accordance with a cross-model ensemble model to generate a cross-model prediction for the predictive task. In some of those embodiments, various cross-model predictions for various predictive tasks are then aggregated to generate cross-task predictions for predictive tasks. Such an arrangement of per-model units, cross-model units, and cross-task predictions provides efficient techniques for addressing predictive model duplicity and predictive task complexity challenges of complex predictive input spaces. In this way, various embodiments of the present invention address efficiency drawbacks resulting from failure of conventional predictive data analysis systems to respond to challenges associated with multiplicity of predictive models as well as structural complexity of predictive tasks.

Generating Cross-Temporal Predictions

FIG. 4 is a flowchart diagram of an example process 400 for generating one or more cross-temporal predictions each corresponding to a predictive task. Through the various steps/operations of process 400, a system of one or more computers can generate cross-temporal predictions by using cross-temporal prediction probabilistic updating (e.g., cross-temporal Bayesian probabilistic updating). Process 400 will now be described with reference to the predictive data analysis computing entity 106 of FIG. 1.

Process 400 begins at step/operation 401 when a cross-temporal unit 114 associated with the predictive task retrieves a cross-temporal model for the predictive task from the cross-temporal configuration data 124, where the cross-temporal model defines a plurality of temporal benchmarks associated with the predictive task including a base temporal benchmark and one or more supplemental temporal benchmarks. In some embodiments, the base temporal benchmark is a current (i.e., prediction time) temporal benchmark and the one or more supplemental temporal benchmarks include one or more historical temporal benchmarks (e.g., a six-months-old historical temporal benchmark, an eight-months-old historical temporal benchmark, a twelve-months-old historical temporal benchmark, a twenty-months-old historical temporal benchmark, etc.).

In some embodiments, the cross-temporal model may define at least one of the following cross-temporal model hyper-parameters for the predictive task: (i) a base temporal benchmark identifier; (ii) a supplemental temporal benchmark count; (iii) supplemental temporal benchmark identifiers for each of the n supplemental temporal benchmarks, where n is equal to the supplemental temporal benchmark count; and (iv) a cross-temporal order of the n supplemental temporal benchmarks which defines a cross-temporal adjustment degree for each supplemental temporal benchmark of the n supplemental temporal benchmarks. For example, the cross-temporal model may define that a current temporal benchmark is the base temporal benchmark, a six-months-old historical temporal benchmark is a first-degree supplemental temporal benchmark, and a twelve-months-old historical temporal benchmark is a second-degree supplemental temporal benchmark.

In some embodiments, at least one of the cross-temporal model hyper-parameters may be determined by utilizing one or more training algorithms. For example, the supplemental temporal benchmark count may be determined based at least in part on a tuned supplemental temporal benchmark count generated by the hyper-parameter unit 116 using a benchmark count hyper-parameter generation model. As another example, at least one of the supplemental temporal benchmark identifiers may be determined based at least in part on one or more tuned supplemental temporal benchmarks generated using a supplemental temporal benchmark identity hyper-parameter generation model. As yet another example, the cross-temporal order may be determined by the hyper-parameter unit 116 using a cross-temporal order hyper-parameter generation model. As a further example, base temporal benchmark identifier may be determined by the hyper-parameter unit 116 using a base temporal benchmark identifier hyper-parameter generation model.

At step/operation 402, the cross-temporal unit 114 retrieves a temporal inference for each temporal benchmark of the plurality of temporal benchmarks, where the temporal inference for a temporal benchmark is a prediction regarding the predictive task based at least in part on prediction input data associated with (e.g., available as of the time of) the temporal benchmark. In some embodiments, the temporal inference for at least one temporal benchmark of the plurality of temporal benchmarks is determined based at least in part on at least one of the following: (i) a cross-task prediction for the predictive task determined based at least in part on prediction input data available at a point in time and/or interval of time defined by the temporal benchmark; (ii) a cross-model prediction for the predictive task determined based at least in part on prediction input data available at a point in time and/or interval of time defined by the temporal benchmark; and (iii) a per-model prediction for the predictive task determined based at least in part on prediction input data available at a point in time and/or interval of time defined by the temporal benchmark.

Generating cross-task predictions, cross-model predictions, and per-model predictions is discussed below with reference to the section related to generating cross-task predictions. While various embodiments of the present invention discuss using cross-task predictions as temporal inferences, a person of ordinary skill in the art will recognize that any prediction technique (including any non-machine-learning-based prediction technique) can be utilized to generate temporal inferences using data available at a point in time and/or interval of time defined by the temporal benchmark.

At step/operation 403, the cross-temporal unit 114 generates the cross-temporal prediction for the predictive task by applying one or more cross-temporal probabilistic updates to the base temporal inference for the base temporal benchmark, where each cross-temporal probabilistic update is associated with a supplemental temporal benchmark of the one or more supplemental temporal benchmarks, and further where each cross-temporal probabilistic update is performed based at least in part on the supplemental temporal inference for a respective supplemental temporal benchmark of the one or more supplemental temporal benchmarks that is associated with the cross-temporal probabilistic update. In some embodiments, the output generation unit 115 displays the cross-temporal prediction using a cross-temporal prediction interface (e.g., a cross-temporal analytics user interface, such as the cross-temporal analytics user interface 700 of FIG. 7 as described below).

In some embodiments, generating the cross-temporal prediction by applying the one or more cross-temporal probabilistic updates includes: (i) for a first-degree supplemental temporal benchmark of the one or more supplemental temporal benchmarks defined based at least in part on the cross-temporal order, generating a partial prediction by updating the temporal inference for the base temporal benchmark in accordance with the temporal inference for the first-degree supplemental temporal benchmark; (ii) for each current successive supplemental temporal benchmark of the one or more supplemental temporal benchmarks other than the first-degree supplemental temporal benchmark, generating a partial prediction by updating the partial prediction for a lower-degree successive supplemental temporal benchmark based at least in part on the temporal inference for the current successive supplemental temporal benchmark; and (iii) generating the cross-temporal prediction based at least in part on the partial prediction for the highest-degree supplemental temporal benchmark of the one or more supplemental temporal benchmarks defined based at least in part on the cross-temporal order.

In some embodiments, the one or more supplemental temporal benchmarks are associated with a cross-temporal order, where the cross-temporal order defines a cross-temporal adjustment degree for each supplemental temporal benchmark. In some embodiments, the cross-temporal probabilistic update for a first-degree supplemental temporal benchmark of the one or more supplemental temporal benchmarks is performed based at least in part on the temporal inference for the base temporal benchmark, and the cross-temporal probabilistic update for each successive supplemental temporal benchmark of the one or more supplemental temporal benchmarks other than the first-degree supplemental temporal benchmark is performed based at least in part on a prior partial prediction for the successive supplemental temporal benchmark, where the prior partial prediction for a particular successive supplemental temporal benchmark is generated based at least in part on the cross-temporal probabilistic update for a lower-degree successive supplemental temporal benchmark.

An operational example of a cross-temporal prediction generation order 500 is presented in FIG. 5. In accordance with the cross-temporal prediction generation order 500, the current temporal benchmark (T) is the base temporal benchmark, the six-months-old historical temporal benchmark (T-6) is the first-degree supplemental temporal benchmark, and the twelve-months-old historical temporal benchmark (T-12) is the second-degree supplemental temporal benchmark. As depicted in the cross-temporal prediction generation order 500, the temporal inference 501 for the base temporal benchmark is used to generate the partial prediction 511 for the base temporal benchmark; the temporal inference 502 for the first-degree supplemental temporal benchmark and the partial prediction 511 for the base temporal benchmark are used to generate the partial prediction 512 for the first-degree supplemental temporal benchmark; and the temporal inference 503 for the second-degree supplemental temporal benchmark and the partial prediction 512 for the first-degree supplemental temporal benchmark are used to generate the cross-temporal prediction 513.

In some embodiments, generating the cross-temporal prediction by applying the one or more cross-temporal probabilistic updates includes performing the operations described by the equation below, where the right-most term is a first partial prediction based at least in part on the temporal inference for the base temporal inference, the second-right-most term is a second partial prediction determined by adjusting the first partial prediction based at least in part on the temporal inference for an example first-degree supplemental temporal benchmark, and the third-right-most term is a third partial prediction determined by adjusting the third partial prediction based at least in part on the temporal inference for an example second-degree supplemental temporal benchmark:

$$\mathbb{P}[D \mid (S_T \cap S_{T-6} \cap S_{T-12})] = \frac{\mathbb{P}[S_{T-12} \mid (D \cap S_T \cap S_{T-6})]}{\mathbb{P}[S_{T-12} \mid (S_T \cap S_{T-6})]} \cdot \qquad \text{Equation 1}$$

$$\frac{\mathbb{P}[S_{T-6} \mid (D \cap S_T)]}{\mathbb{P}[S_{T-6} \mid S_T]} \cdot \frac{\mathbb{P}[S_T \mid D]}{\mathbb{P}[S_T]} \cdot \mathbb{P}[D]$$

While the example equation depicted above shows two cross-temporal probabilistic updates each associated with one of two supplemental temporal benchmarks, a person of ordinary skill in the relevant technology will recognize that any number of cross-temporal probabilistic updates associated with any number of supplemental temporal benchmarks may be utilized.

In some embodiments, the predictive task is related to a disease risk score prediction task. In some embodiments, the output generation unit 115 generates a cross-temporal analytics user interface for the predictive task based at least in part on the cross-temporal prediction for the predictive task. In some of those embodiments, to generate the cross-temporal analytics user interface, the output generation unit 115 performs operations of process 600 depicted in FIG. 6.

As depicted in FIG. 6, process 600 begins at step/operation 601 when the output generation unit 115 generates a temporal distribution for the predictive task, which may be a distribution of temporal inferences across the plurality of temporal benchmarks. At step/operation 602, the output generation unit 115 generates a cross-temporal distribution, which may be a distribution of partial predictions determined using cross-temporal probabilistic updates across the plurality of temporal benchmarks. At step/operation 603, the output generation unit 115 generates the cross-temporal analytics user interface based at least in part on the temporal distribution and the cross-temporal distribution.

An operational example of a cross-temporal analytics user interface 700 is presented in FIG. 7. As depicted in FIG. 7, cross-temporal analytics user interface 700 depicts a cross-temporal analytics visualization which includes, for each predictive task represented by rows of the cross-temporal analytics visualization, the temporal distribution represented by columns 701 of the cross-temporal analytics visualization and the cross-temporal distribution represented by columns 702 of the cross-temporal analytics visualization.

Generating Cross-Task Predictions

FIG. 8 is a data flow diagram of an example process 800 for generating one or more cross-task predictions 803 each corresponding to a predictive task. Through the various steps/operations of process 800, a system of one or more computers can generate cross-task predictions by using cross-task prediction probabilistic updating (e.g., Bayesian probabilistic updating). Process 800 will now be described with reference to the predictive data analysis computing entity 106 of FIG. 1.

As depicted in FIG. 8, the process 800 begins when each per-model units 111A-I of the predictive data analysis computing entity 106 generates a per-model inference 801 for a corresponding predictive task associated with the per-model unit 111A-I by applying a corresponding predictive model associated with the per-model unit 111A-I to one or more predictive inputs. In some embodiments, a particular per-model unit 111A-I is configured to: (i) retrieve (e.g., from an external computing entity 102) one or more predictive inputs for the particular per-model unit 111A-I (e.g., patient data associated with a particular patient); (ii) retrieve (e.g., from the per-model configuration data 121 stored in the storage subsystem 108) a particular predictive model (e.g., a neural network predictive model) associated with the particular per-model unit 111A-I; and (iii) apply the particular predictive model to the one or more predictive inputs to generate a per-model inference 801 (e.g., a neural network cancer disease prediction) for a predictive task (e.g., a cancer prediction predictive task).

For example, as depicted in FIG. 8, each of the per-model units A-C 111A-C may be configured to apply a corresponding predictive model to one or more predictive inputs to generate a per-model inference 801 associated with a cancer prediction predictive task. As another example, each of the per-model units D-E 111D-E may be configured to apply a corresponding predictive model to one or more predictive inputs to generate a per-model inference 801 associated with an Alzheimer's disease prediction predictive task. As yet another example, each of the per-model units G-I 111G-I may be configured to apply a corresponding predictive model to one or more predictive inputs to generate a per-model inference 801 associated with Crohn's disease prediction predictive task.

While not depicted in FIG. 8, a person of ordinary skill in the art will recognize that at least some of the per-model units 111A-I may be associated with the same predictive model. For example, each of the per-model units A 111A, D 111D, and G 111G may be associated with a particular neural network predictive model, where the per-model unit A 111A is configured to apply the particular neural network predictive model to one or more predictive inputs to generate a per-model inference 801 associated with a cancer prediction predictive task, the per-model unit D 111D is configured to apply the particular neural network predictive model to one or more predictive inputs to generate a per-model inference 801 associated with an Alzheimer's disease predictive task, and the per-model unit G 111G is configured to apply the particular neural network predictive model to one or more predictive inputs to generate a per-model inference 801 associated with a Crohn's disease predictive task. As another example, each of the per-model units B 111B, E 111E, and H 111H may be associated with a particular Bayesian network predictive model, where the per-model unit B 111B is configured to apply the particular Bayesian network predictive model to one or more predictive inputs to generate a per-model inference 801 associated with a cancer prediction predictive task, the per-model unit E 111E is configured to apply the particular Bayesian network predictive model to one or more predictive inputs to generate a per-model inference 801 associated with an Alzheimer's disease predictive task, and the per-model unit H 111H is configured to apply the particular Bayesian network predictive model to one or more predictive inputs to generate a per-model inference 801 associated with a Crohn's disease predictive task. As a further example, each of the per-model units C 111C, F 111F, and I 111I may be associated with a particular decision tree predictive model, where the per-model unit C 111C is configured to apply the particular decision tree predictive model to one or more predictive inputs to generate a per-model inference 801 associated with a cancer prediction predictive task, the per-model unit F 111F is configured to apply the particular decision tree predictive model to one or more predictive inputs to generate a per-model inference 801 associated with an Alzheimer's disease predictive task, and the per-model unit I 111I is configured to apply the particular decision tree predictive model to one or more predictive inputs to generate a per-model inference 801 associated with a Crohn's disease predictive task.

The process 800 continues when each per-model unit 111A-I provides its generated per-model inference 801 to a cross-model unit 112A-C associated with the per-model unit 111A-I. In particular, the per-model units A-C 111A-C provide their generated per-model inferences 801 to the cross-model unit A 112A, the per-model units D-F 111D-F provide their generated per-model inferences 801 to the cross-model unit B 112B, and the per-model units G-I 111G-I provide their generated per-model inferences 801 to the cross-model unit C 112C. In some embodiments, a particular cross-model unit 112A-C is configured: (i) retrieve (e.g., from the per-model units 111A-I) particular per-model inferences 801 for a particular predictive task associated with the particular cross-model unit 112A-C, (ii) retrieve (e.g., from the cross-model configuration data 122 stored in the storage subsystem 108) a particular cross-model ensemble model associated with the particular predictive task, and (iii) apply the particular cross-model ensemble model to the particular per-model inferences 801 for the particular predictive task to generate a cross-model prediction 802 for the particular predictive task.

In some embodiments, each cross-model unit 112A-C is associated with a corresponding predictive task and is configured to process one or more per-model inferences associated with the corresponding predictive task to generate a cross-model prediction 802 for the corresponding predictive task. For example, the cross-model unit A 112A may be associated with a cancer prediction predictive task and may be configured to process per-model inferences 801 associated with the cancer prediction predictive task (e.g., per-model inferences 801 generated by the per-model units A-C 111A-C) to generate a cross-model prediction 802 for the cancer prediction predictive task. As another example, the cross-model unit B 112B may be associated with an Alzheimer's disease prediction predictive task and may be configured to process per-model inferences 801 associated with the cancer prediction predictive task (e.g., per-model inferences 801 generated by the per-model units D-F 111D-F) to generate a cross-model prediction 802 for the Alzheimer's disease prediction predictive task. As a further example, the cross-model unit C 112C may be associated with a Crohn's disease prediction predictive task and may be configured to process per-model inferences 801 associated with the Crohn's disease prediction predictive task (e.g., per-model inferences 801 generated by the per-model units G-I 111G-I) to generate a cross-model prediction 802 for the Crohn's disease prediction predictive task.

In some embodiments, to generate a particular cross-model prediction 802 for a particular predictive task, a particular cross-model unit 112A-C may perform the various steps/operations of the example process 900 depicted in FIG. 9. The process 900 begins at step/operation 901 when the particular cross-model unit 112A-C retrieves particular per-model inferences 801 for the particular predictive task. For example, the particular cross-model unit 112A-C may retrieve a particular per-model inference 801 associated with the particular predictive task that is generated by a per-model unit 111A-I for a neural network predictive model, a particular per-model inference 801 associated with the particular predictive task that is generated by a per-model unit 111A-I for a Bayesian network predictive model, a particular per-model inference 801 associated with the particular predictive task that is generated by a per-model unit 111A-I for a decision tree network predictive model, a particular per-model inference 801 associated with the particular predictive task that is generated by a per-model unit 111A-I for a random forest network predictive model, etc. A particular per-model inference 801 may correspond to a probability value characterized by $P(D_m|m_n)$, where $D_m$ is the particular predictive task for the particular per-model inference and $m_n$ is an output of a particular predictive model associated with the particular per-model inference.

At step/operation 902, the particular cross-model unit 112A-C identifies a base inference from the particular per-model inferences 801 retrieved in step/operation 901. For example, the particular cross-model unit 112A-C may identify a particular per-model inference 801 generated based at least in part on a default predictive model for the particular predictive task as the base inference for the particular predictive task. In another example, the particular cross-model unit 112A-C may identify a randomly-selected per-model inference 801 as the base inference for the particular predictive task.

At step/operation 903, the particular cross-model unit 112A-C generates one or more cross-model updates for the base inference. In some embodiments, the particular cross-model unit 112A-C generates a cross-model order for the particular per-model inferences 801 retrieved in step/operation 901, where the cross-model order identifies a cross-model degree for each particular per-model inference 801 including a lowest cross-model degree for the base inference. Then, for each first particular per-model inference 801 other than the base inference which has a corresponding first cross-model degree in the cross-model order, the particular cross-model unit 112A-C generates a first cross-model update that relates a partial cross-model prediction 802 determined based at least in part on the base inference and based at least in part on each particular per-model inference 801 having a lower cross-model degree than the first cross-model degree to a final cross-model prediction 802 based at least in part on the first particular per-model inference 801. For example, given a set of per-model inferences 801 {$IN_1$, $IN_2$, $IN_3$, $IN_4$} having the cross-model order {$IN_1 \rightarrow IN_2 \rightarrow IN_3 \rightarrow IN_4$} where $IN_1$ is the base inference, the particular cross-model unit 112A-C may generate a first cross-model update that relates $IN_1$ to the final cross-model prediction 802 based at least in part on $IN_2$, a second cross-model update that relates the first cross-model update to the final cross-model prediction 802 based at least in part on $IN_3$, and a third cross-model update that relates the second cross-model update to the final cross-model prediction 802 based at least in part on $IN_4$.

At step/operation 904, the particular cross-model unit 112A-C generates the cross-model prediction 802 based at least in part on the base inference identified in step/operation 902 and the one or more cross-model updates generated in step/operation 903. For example, the particular cross-model unit 112A-C may generate a cross-model prediction 802 $P(D_1|m_1, m_2)$ for a predictive task $D_1$ based at least in part on the per-model inferences 801 $P(D_1|m_1)$ and $P(D_1|m_2)$ by performing steps/operations corresponding to the equation:

$$P(D_1 \mid m_1, m_2) = \frac{P(m_2 \mid D_1 \cap m_1)}{P(m_2 \mid m_1)} * P(D_1 \mid m_1),$$

where the latter term is the base inference, the former term is the cross-model update for the non-base inference $P(D_1|m_2)$, and $m_1$ and $m_2$ are outputs of particular predictive models associated with the per-model inferences $P(D_1|m_1)$–$P(D_2|m_2)$ respectively. As another example, the particular cross-model unit 112A-C may generate a cross-model prediction 802 $P(D_1|m_1, m_2, m_3)$ for a predictive task $D_1$ based at least in part on the per-model inferences 801 $P(D_1|m_1)$, $P(D_1|m_2)$, and $P(D_1|m_3)$ by performing steps/operations corresponding to the equation:

$$P(D1 \mid m1, m2, m3) = \frac{P(m_3 \mid D_1 \cap m_1 \cap m_2)}{P(m_3 \mid m_1 \cap m_2)} * \frac{P(m_2 \mid D_1 \cap m_1)}{P(m_2 \mid m_1)} * P(D_1 \mid m_1),$$

where the latter term is the base inference, the former two terms are the cross-model updates for the non-base inference $P(D_1|m_3)$ and $P(D_1|m_2)$ respectively, and $m_1$-$m_3$ are outputs of particular predictive models associated with the per-model inferences $P(D_1|m_1)$–$P(D_2|m_3)$ respectively.

In some embodiments, the per-model inferences 801 and the cross-model updates are determined based at least in part on a cross-model distribution, such as the cross-model distribution 1000 of FIG. 10. The cross-model distribution 1000 is associated with two per-model inferences, i.e., a per-model inference A whose range is represented by the per-model inference space A 1001A and a per-model inference B whose range is represented by the per-model inference space B 1001B. The cross-model distribution 1000 also includes a third dimension associated with the cross-model prediction space 1002, which indicates a cross-model prediction for each combination of a particular value for the per-model inference A and a particular value for the per-model inference B. In some embodiments, a cross-model distribution such as the cross-model distribution 1000 is stored on the storage subsystem 108 as part of the cross-model configuration data 122.

Returning to FIG. 8, the process 800 continues when the cross-task unit 113 retrieves the cross-model predictions 802 to generate one or more cross-task predictions 803. A cross-task prediction 803 may be a prediction for a first predictive task given a prediction (e.g., a cross-model prediction 802) for each of one or more other predictive tasks. In some embodiments, the cross-task predictions 803 include one or more multi-morbidity predictions, i.e., a prediction about presence of one or more diseases (e.g., a single disease and/or a combination of diseases) given one or more related disease predictions, wherein each related disease prediction is about presence of one or more related diseases (e.g., a single related disease and/or a combination of related diseases). Examples of multi-morbidity predictions may include a prediction for a cancer prediction predictive task given a prediction for an Alzheimer's disease prediction predictive task and/or a prediction for a Crohn's disease prediction predictive task; a prediction for an Alzheimer's disease prediction predictive task given a prediction for a cancer disease prediction predictive task and/or a Crohn's disease prediction predictive task; a prediction for a Crohn's disease prediction predictive task given a prediction for a cancer disease prediction predictive task and/or an Alzheimer's disease prediction predictive task; a prediction for a prediction task associated with presence of both cancer and Alzheimer's disease given a prediction for a Crohn's disease prediction predictive task and/or a leukemia prediction predictive task; etc.

In some embodiments, to generate a particular cross-task prediction 803 for a particular predictive task, the cross-task unit 113 may perform the various steps/operations of the process 1100 depicted in FIG. 11. The process 1100 depicted in FIG. 11 begins at step/operation 1101 when the cross-task unit 113 retrieves cross-model predictions 802 for multiple predictive tasks. For example, the cross-task unit 113 may retrieve a first cross-model prediction associated with a cancer prediction predictive task, a second cross-model prediction associated with an Alzheimer's disease prediction predictive task, a third cross-model prediction associated with a Crohn's disease prediction predictive task, etc. A cross-model prediction 802 for a particular predictive task may correspond to a probability value characterized by $P(D_1|m_1 \ldots m_n)$, where $D_1$ corresponds to the particular predictive task, $m_1 \ldots m_n$ correspond to outputs of particular predictive models, and n may be two or more.

At step/operation 1102, the cross-task unit 113 identifies a base prediction from the cross-model predictions 802 retrieved in step/operation 1101. For example, where the particular cross-model prediction 802 is associated with a particular predictive task, the cross-task unit 113 may identify the cross-model prediction 802 associated with the particular predictive task as the base prediction from the cross-model predictions 802.

At step/operation 1103, the cross-task unit 113 generates one or more cross-task prediction updates for the base prediction. In some embodiments, the particular cross-model unit 112A-C generates a cross-task prediction order for the cross-model predictions 802 retrieved in step/operation 1101, where the cross-task prediction order identifies a cross-task prediction degree for each particular cross-model prediction 802 including a lowest cross-model degree for the base prediction. Then, for each cross-model prediction 802 other than the base prediction which has a corresponding first cross-task prediction degree in the cross-task prediction order, the particular cross-model unit 112A-C generates a first cross-task prediction update that relates a partial cross-task prediction 803 determined based at least in part on the base prediction and based at least in part on each cross-model prediction 802 having a lower cross-task prediction degree than the first cross-task prediction degree to a final cross-task prediction 803 based at least in part on the first cross-model prediction 802. For example, given a set of cross-model prediction 802 $\{CP_1, CP_2, CP_3, CP_4\}$ having the cross-task prediction order $\{CP_1 \rightarrow CP_2 \rightarrow CP_3 \rightarrow CP_4\}$ where $CP_4$ is the base prediction, the cross-task unit 113 may generate a first cross-task prediction update that relates $CP_1$ to the final cross-task prediction 803 based at least in part on $CP_2$, a second cross-task prediction update that relates the first cross-task prediction update to final cross-task prediction 803 based at least in part on $CP_3$, and a third cross-task prediction update that relates the second cross-task prediction update to the final cross-task prediction 803 based at least in part on $CP_4$.

At step/operation 1104, the cross-task unit 113C generates the cross-task prediction 803 based at least in part on the base prediction identified in step/operation 1102 and the one or more cross-task prediction updates generated in step/operation 1103. For example, the cross-task unit 113C may generate a cross-task prediction 803 $P(D_1|m_1, m_2, D_2)$ for a predictive task D1 based at least in part on the per-model inferences 801 $P(D_1|m_1)$ and $P(D_2|m_2)$, the cross-model prediction 802 $P(D_1|m_1, m_2)$, and a cross-model prediction 802 for the predictive task D2 by performing steps/operations corresponding to the equation:

$$P(D_1 \mid m_1, m_2, D_2) = \frac{P(D_2 \mid D_1 \cap m_1 \cap m_2)}{P(D_2 \mid m_1 \cap m_2)} * P(D_1 \mid m_1, m_2),$$

where the latter term is the base prediction, the former term is the cross-task prediction update corresponding to the predictive task $D_2$, and $m_1$ and $m_2$ are outputs of particular predictive models associated with the predictive task $D_1$. As another example, the cross-task unit 113C may generate a cross-task prediction 803 $P(D_1|m_1, m_2, D_2, D_3)$ for a predictive task $D_1$ based at least in part on the per-model inferences 801 $P(D_1|m_1)$ and $P(D_2|m_2)$, the cross-model prediction 802 $P(D_1|m_1, m_2)$, a cross-model prediction 802 for the predictive task D2, and a cross-model prediction 802 for the predictive task D3 by performing steps/operations corresponding to the equation:

$$P(D1 \mid m1, m2, D2, D3) = \frac{P(D_3 \mid D_1 \cap m_1 \cap m_2 \cap D_2)}{P(D_3 \mid m_1 \cap m_2 \cap D_2)} * \frac{P(D_2 \mid D_1 \cap m_1 \cap m_2)}{P(D_2 \mid m_1 \cap m_2)} * P(D_1 \mid m_1, m_2),$$

where the latter term is the base prediction, the former two terms are the cross-task prediction updates corresponding to the predictive tasks D2 and D3, and m1 and m2 are outputs of particular predictive models associated with the predictive task $D_1$. As a further example, the cross-task unit 113C generates the cross-task prediction 803 $P[W|(S_{D_1} \cap S_{D_2} \cap S_{D_3})]$, which describes the probability of event W given three disease scores $S_{D_1}$, $S_{D_2}$, and $S_{D_3}$ by performing steps/operations corresponding to the equation:

$$P[W \mid (S_{D_1} \cap S_{D_2} \cap S_{D_3})] = \frac{\mathbb{P}[S_{D_3} \mid (W \cap S_{D_1} \cap S_{D_2})]}{\mathbb{P}[S_{D_3} \mid (S_{D_1} \cap S_{D_2})]} \cdot \frac{\mathbb{P}[S_{D_2} \mid (W \cap S_{D_1})]}{\mathbb{P}[S_{D_2} \mid S_{D_1}]} \cdot \mathbb{P}[W \mid S_{D_1}],$$

where the latter term is the base prediction and the former two terms are cross-task prediction updates.

In some embodiments, the cross-model predictions 802 and the cross-task prediction updates are determined based at least in part on a cross-task prediction distribution, such as the cross-task prediction distribution 1200 of FIG. 12. The cross-task prediction distribution 1200 is associated with two cross-model predictions, i.e., a cross-model prediction A whose range is represented by the cross-model prediction space A 1201A and a cross-model prediction B whose range is represented by the cross-model prediction space B 1201B. The cross-task prediction distribution 1200 also includes a third dimension associated with the cross-task prediction space 1202, which indicates a cross-task prediction for each combination of a particular value for the cross-model prediction A and a particular value for the cross-model prediction B. In some embodiments, a cross-task prediction distribution such as the cross-task prediction distribution 1200 is stored on the storage subsystem 108 as part of the cross-task configuration data 123.

FIG. 13 is a flowchart diagram of an example process 1300 for generating representational conclusions based at least in part on cross-task prediction visual representations. Via the various steps/operations of process 1300, a system of one or more computers can generate visual representations that are indicative of relationships between various predictions for various predictive tasks and utilize the noted visual representations to derive important insights about underlying cross-task prediction distributions. The process 1300 will now be described with reference to the predictive data analysis computing entity 106 of FIG. 1.

The process 1300 begins at step/operation 1301 when the predictive data analysis computing entity 106 generates an initial cross-task prediction distribution for two or more prediction input entities. In some embodiments, the predictive data analysis computing entity 106 identifies the two or more prediction input entities (e.g., two or more patients) and retrieves, for each prediction input entity, one or more cross-task predictions, where the one or more cross-task predictions for each prediction input entity relate to one or more predictive tasks associated with the initial cross-task prediction distribution. For example, for each patient, the predictive data analysis computing entity 106 may generate a cross-task prediction characterizing a cancer multi-morbidity prediction for the patient, an Alzheimer's disease multi-morbidity prediction for the patient, a Crone's disease multi-morbidity prediction for the patient, a cancer-plus-Alzheimer's-disease multi-morbidity prediction for the patient, a cancer-minus-Alzheimer's-disease multi-morbidity prediction for the patient, etc. In some embodiments, the initial cross-task prediction distribution is characterized by a cross-task prediction distribution space, where the cross-task prediction distribution space may be an n-dimensional space and n may be equal to a number of cross-distributions associated with the cross-task prediction distribution. In some embodiments, a particular disease may be associated with two or more prediction tasks. For example, cancer may be associated with a cancer-presence prediction, a cancer-absence prediction, a cancer-and-Alzheimer's disease prediction, a cancer-but-not-Alzheimer's disease prediction, etc.

At step/operation 1302, the predictive data analysis computing entity 106 generates a cross-task prediction visual representation based at least in part on the initial cross-task prediction distribution space generated in step/operation 1302. In some embodiments, the predictive data analysis computing entity 106 projects the initial cross-task prediction distribution into a cross-task prediction representation space to generate an updated cross-task prediction distribution having a cross-task prediction representation space, where the cross-task prediction representation space may be an m-dimensional space and m may be lower than dimensions of the cross-task prediction distribution space associated with the initial cross-task prediction distribution space. In some embodiments, to project the initial cross-task prediction distribution into the cross-task prediction representation space, the predictive data analysis computing entity 106 performs dimensionality reduction. In some embodiments, the predictive data analysis computing entity 106 generates the cross-task prediction visual representation based at least in part on the updated cross-task prediction distribution.

FIG. 14 provides an operational example of a cross-task prediction visual representation 1400. The example cross-task prediction visual representation 1400 is associated with a cross-task prediction representation space having four cross-task prediction representation dimensions, i.e., three geometric cross-task prediction representation dimensions (i.e., an x-dimension, a y-dimension, and a z-dimension) as well as a cross-task prediction representation dimension identified by the color distinctions. The four cross-task prediction representation dimensions present a measure of cross-predictive distance between various prediction input entities. In some embodiments, each point in the example cross-task prediction visual representation 1400 may correspond to a patient, and the color of each point may indicate the predominant disease prediction for the corresponding patient. In some of those embodiments, the geometric distance between the points may indicate measure of cross-predictive distances between patients having different predominant disease predictions. For example, the cross-task prediction visual representation 1400 may indicate multi-morbidity similarities between malaria patients and cancer patients.

At step/operation 1303, the predictive data analysis computing entity 106 generates one or more representational conclusions based at least in part on the cross-task prediction visual representation generated in step/operation 1302. In some embodiments, the predictive data analysis computing entity 106 generates one or more representational metrics based at least in part on the cross-task prediction visual representation and generates the representational conclusions based at least in part on the one or more representational metrics. In some embodiments, at least some of the representational metrics are each determined based at least in part on a difference between at least two values identified by the cross-task prediction visual representation, for example a difference between geometric coordinates for two or more prediction input entities represented by the cross-task prediction visual representation. In some embodiments, at least some of the representational metrics describe the updated cross-task prediction distribution associated with the cross-task prediction visual representation. In some embodiments, at least some of the representational metrics are determined using one or more computational geometry routines. In some embodiments, at least some of the representational conclusions describe multi-morbidity conclusions across a population of patients.

In some embodiments, the predictive data analysis computing entity 106 generates one or more reports and/or performs one or more actions based at least in part on the representational conclusions. For example, given a representational conclusion that cancer patients have a higher propensity for another disease, the predictive data analysis computing entity 106 may schedule tests and/or visitations for cancer patients intended to determine whether the cancer patients have the other disease. As another example, given a representational conclusion that cancer patients have a higher propensity for another disease, the predictive data analysis computing entity 106 may generate alerts for physicians of the cancer patients noting the discovered relationship. As a further example, the predictive data analysis computing entity 106 may generate multi-morbidity reports indicating discoveries about relationships between various diseases and conditions, such as reports associated with individual patients and/or reports for entire segments of patients.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for generating a cross-temporal prediction for a predictive task, the computer-implemented method comprising:
   generating, by one or more processors, a plurality of temporal inferences for the predictive task, wherein: (i) each temporal inference is associated with a temporal benchmark of a plurality of temporal benchmarks, (ii) the temporal inference is a prediction based at least in part on input data available at a time defined by the associated temporal benchmark, (iii) the plurality of temporal benchmarks comprises a base temporal benchmark and one or more supplemental temporal benchmarks, (iv) the base temporal benchmark is associated with a base temporal inference of the plurality of temporal inferences, and (v) each supplemental temporal benchmark is associated with a corresponding supplemental temporal inference of one or more supplemental temporal inferences of the plurality of temporal inferences;

generating, by a cross-temporal unit executing on the one or more processors, the cross-temporal prediction for the predictive task, wherein the cross-temporal prediction is a combination of the base temporal inference of the plurality of temporal inferences and the one or more supplemental temporal inferences of the plurality of temporal inferences, wherein the cross-temporal prediction is generated by adjusting the base temporal inference of the plurality of temporal inferences based at least in part on the one or more supplemental temporal inferences of the plurality of temporal inferences via one or more cross-temporal probabilistic updates, wherein: (i) each cross-temporal probabilistic update is associated with a supplemental temporal benchmark of the one or more supplemental temporal benchmarks, and (ii) each cross-temporal probabilistic update is performed based at least in part on the supplemental temporal inference for a respective supplemental temporal benchmark of the one or more supplemental temporal benchmarks associated with the cross-temporal probabilistic update; and providing, by the one or more processors, the cross-temporal prediction for display using a cross-temporal prediction interface.

2. The computer-implemented method of claim 1, wherein the predictive task is a disease risk score prediction task.

3. The computer-implemented method of claim 1, wherein:
the one or more supplemental temporal benchmarks are associated with a cross-temporal order,
the cross-temporal order defines a cross-temporal adjustment degree for each supplemental temporal benchmark,
the cross-temporal probabilistic update for a first-degree supplemental temporal benchmark of the one or more supplemental temporal benchmarks is performed based at least in part on the temporal inference for the base temporal benchmark,
the cross-temporal probabilistic update for each successive supplemental temporal benchmark of the one or more supplemental temporal benchmarks other than the first-degree supplemental temporal benchmark is performed based at least in part on a prior partial prediction for the successive supplemental temporal benchmark, and
the prior partial prediction for a particular successive supplemental temporal benchmark is generated based at least in part on the cross-temporal probabilistic update for a lower-degree successive supplemental temporal benchmark.

4. The computer-implemented method of claim 1, wherein:
the one or more supplemental temporal benchmarks comprise a tuned number of supplemental temporal benchmarks, and
the tuned number of supplemental temporal benchmarks is generated using a hyper-parameter generation model.

5. The computer-implemented method of claim 1, wherein:
the one or more supplemental temporal benchmarks comprise one or more tuned supplemental temporal benchmarks,
the one or more tuned supplemental temporal benchmarks are generated using a hyper-parameter generation model.

6. The computer-implemented method of claim 1, wherein the base temporal benchmark is a current temporal benchmark and the one or more supplemental temporal benchmarks are one or more historical temporal benchmarks.

7. The computer-implemented method of claim 1, wherein: (i) the predictive task is one of a plurality of related predictive tasks, and (ii) generating a first temporal inference of the plurality of temporal inferences that is associated with a first temporal benchmark of the plurality of temporal benchmarks comprises:
receiving, for each related predictive task of the plurality of related predictive tasks, a plurality of per-model inferences with respect to the first temporal benchmark, wherein each per-model inference of the plurality of per-model inferences associated with a related predictive task of the plurality of related predictive tasks is determined based at least in part on a predictive model of a plurality of predictive models for the per-model inference;
generating, for each related predictive task of the plurality of related predictive tasks, a cross-model prediction with respect to the first temporal benchmark based at least in part on the plurality of per-model inferences for the related predictive task;
generating, based at least in part on each cross-model prediction associated with a related predictive task of the plurality of related predictive tasks, a cross-task prediction for the predictive task with respect to the first temporal benchmark, wherein: (i) determining the cross-task prediction comprises applying one or more cross-task probabilistic updates to the cross-model prediction for the predictive task, and (ii) each cross-task probabilistic update of the one or more cross-task probabilistic updates is determined based at least in part on the cross-model prediction for a corresponding related predictive task of the one or more related predictive tasks associated with the cross-task probabilistic update; and
generating the first temporal inference based at least in part on the cross-task prediction.

8. The computer-implemented method of claim 1, wherein: (i) each cross-temporal probabilistic update is configured to generate a temporal prediction for a corresponding supplemental temporal benchmark of the one or more supplemental temporal benchmarks associated with the cross-temporal probabilistic update, and (ii) the computer-implemented method further comprises:
generating a temporal distribution for the predictive task based at least in part on each temporal inference of the plurality of temporal inferences;
generating a cross-temporal distribution for the predictive task based at least in part on each partial prediction for a temporal benchmark of the plurality of benchmarks; and
generating a cross-temporal analytics user interface based at least in part on the temporal distribution and the cross-temporal distribution.

9. A non-transitory computer storage medium for generating a cross-temporal prediction for a predictive task, the non-transitory computer storage medium comprising instructions configured to cause one or more processors to at least at least perform operations configured to at least:

generate a plurality of temporal inferences for the predictive task, wherein: (i) each temporal inference is associated with a temporal benchmark of a plurality of temporal benchmarks, (ii) the temporal inference is a prediction based at least in part on input data available at a time defined by the associated temporal benchmark, (iii) the plurality of temporal benchmarks comprises a base temporal benchmark and one or more supplemental temporal benchmarks, (iv) the base temporal benchmark is associated with a base temporal inference of the plurality of temporal inferences, and (v) each supplemental temporal benchmark is associated with a corresponding supplemental temporal inference of one or more supplemental temporal inferences of the plurality of temporal inferences;

generate, by a cross-temporal unit executing on the one or more processors, the cross-temporal prediction for the predictive task, wherein the cross-temporal prediction is a combination of the base temporal inferences of the plurality of temporal inferences and the one or more supplemental temporal inferences of the plurality of temporal inferences, wherein the cross-temporal prediction is generated by adjusting the base temporal inference of the plurality of temporal inferences based at least in part on the one or more supplemental temporal inferences of the plurality of temporal inferences via one or more cross-temporal probabilistic updates, wherein: (i) each cross-temporal probabilistic update is associated with a supplemental temporal benchmark of the one or more supplemental temporal benchmarks, and (ii) each cross-temporal probabilistic update is performed based at least in part on the supplemental temporal inference for a respective supplemental temporal benchmark of the one or more supplemental temporal benchmarks associated with the cross-temporal probabilistic update; and provide the cross-temporal prediction for display using a cross-temporal prediction interface.

10. The non-transitory computer storage medium of claim 9, wherein the predictive task is a disease risk score prediction task.

11. The non-transitory computer storage medium of claim 9, wherein:

the one or more cross-temporal probabilistic updates are associated with a cross-temporal order, the cross-temporal order defines a prior cross-temporal probabilistic update for each current cross-temporal probabilistic update of the one or more cross-temporal probabilistic updates, and each current cross-temporal probabilistic update of the one or more cross-temporal probabilistic updates relates a prior temporal prediction generated in accordance with a prior cross-temporal probabilistic update to a current temporal prediction generated in accordance with the current cross-temporal probabilistic update.

12. The non-transitory computer storage medium of claim 9, wherein:

the one or more supplemental temporal benchmarks comprise a tuned number of supplemental temporal benchmarks, and the tuned number of supplemental temporal benchmarks is generated using a hyper-parameter generation model.

13. The non-transitory computer storage medium of claim 9, wherein:

the one or more supplemental temporal benchmarks comprise one or more tuned supplemental temporal benchmarks, the one or more tuned supplemental temporal benchmarks are generated using a hyper-parameter generation model.

14. An apparatus for generating a cross-temporal prediction for a predictive task, the apparatus comprising at least one processor and at least one non-transitory memory comprising program code, wherein the at least one non-transitory memory and the program code are configured to, with the at least one processor, cause the apparatus to perform operations configured to at least:

generate a plurality of temporal inferences for the predictive task, wherein: (i) each temporal inference is associated with a temporal benchmark of a plurality of temporal benchmarks, (ii) the temporal inference is a prediction based at least in part on input data available at a time defined by the associated temporal benchmark, (iii) the plurality of temporal benchmarks comprises a base temporal benchmark and one or more supplemental temporal benchmarks, (iv) the base temporal benchmark is associated with a base temporal inference of the plurality of temporal inferences, and (v) each supplemental temporal benchmark is associated with a corresponding supplemental temporal inference of one or more supplemental temporal inferences of the plurality of temporal inferences;

generate, by a cross-temporal unit executing on the at least one processor, the cross-temporal prediction for the predictive task, wherein the cross-temporal prediction is a combination of a base temporal inference of the plurality of temporal inferences and the one or more supplemental temporal inferences of the plurality of temporal inferences, wherein the cross-temporal prediction is generated by adjusting the base temporal inference of the plurality of temporal inferences based at least in part on the one or more supplemental temporal inferences of the plurality of temporal inferences via one or more cross-temporal probabilistic updates, wherein: (i) each cross-temporal probabilistic update is associated with a supplemental temporal benchmark of the one or more supplemental temporal benchmarks, and (ii) each cross-temporal probabilistic update is performed based at least in part on the supplemental temporal inference for a respective supplemental temporal benchmark of the one or more supplemental temporal benchmarks associated with the cross-temporal probabilistic update; and provide the cross-temporal prediction for display using a cross-temporal prediction interface.

15. The apparatus of claim 14, wherein the predictive task is a disease risk score prediction task.

16. The apparatus of claim 14, wherein:

the one or more supplemental temporal benchmarks are associated with a cross-temporal order, the cross-temporal order defines a cross-temporal adjustment degree for each supplemental temporal benchmark, the cross-temporal probabilistic update for a first-degree supplemental temporal benchmark of the one or more supplemental temporal benchmarks is performed based at least in part on the temporal inference for the base temporal benchmark, the cross-temporal probabilistic update for each successive supplemental temporal benchmark of the one or more supplemental temporal benchmarks other than the first-degree supplemental temporal benchmark is performed based at least in part on a prior partial prediction for the successive supplemental temporal benchmark, and the prior partial prediction for a particular successive supplemental temporal benchmark is generated based at least in part on the cross-temporal probabilistic update for a lower-degree successive supplemental temporal benchmark.

17. The apparatus of claim 14, wherein:

the one or more supplemental temporal benchmarks comprise a tuned number of supplemental temporal benchmarks, and the tuned number of supplemental temporal benchmarks is generated using a hyper-parameter generation model.

18. The apparatus of claim 14, wherein:

the one or more supplemental temporal benchmarks comprise one or more tuned supplemental temporal benchmarks, the one or more tuned supplemental temporal benchmarks are generated using a hyper-parameter generation model.

19. The apparatus of claim 14, wherein the base temporal benchmark is a current temporal benchmark and the one or more supplemental temporal benchmarks are one or more historical temporal benchmarks.

20. The apparatus of claim 14, wherein: (i) the predictive task is one of a plurality of related predictive tasks, and (ii) generating a first temporal inference of the plurality of temporal inferences that is associated with a first temporal benchmark of the plurality of temporal benchmarks comprises:

receiving, for each related predictive task of the plurality of related predictive tasks, a plurality of per-model inferences with respect to the first temporal benchmark, wherein each per-model inference of the plurality of per-model inferences associated with a related predictive task of the plurality of related predictive tasks is determined based at least in part on a predictive model of a plurality of predictive models for the per-model inference;

generating, for each related predictive task of the plurality of related predictive tasks, a cross-model prediction with respect to the first temporal benchmark based at least in part on the plurality of per-model inferences for the related predictive task;

generating, based at least in part on each cross-model prediction associated with a related predictive task of the plurality of related predictive tasks, a cross-task prediction for the predictive task with respect to the first temporal benchmark, wherein: (i) determining the cross-task prediction comprises applying one or more cross-task probabilistic updates to the cross-model prediction for the predictive task, and (ii) each cross-task probabilistic update of the one or more cross-task probabilistic updates is determined based at least in part on the cross-model prediction for a corresponding related predictive task of the one or more related predictive tasks associated with the cross-task probabilistic update; and generating the first temporal inference based at least in part on the cross-task prediction.

* * * * *

UNITED STATES PATENT AND TRADEMARK OFFICE
CERTIFICATE OF CORRECTION

PATENT NO. : 11,645,565 B2
APPLICATION NO. : 16/680785
DATED : May 9, 2023
INVENTOR(S) : Michael J. McCarthy et al.

Page 1 of 1

It is certified that error appears in the above-identified patent and that said Letters Patent is hereby corrected as shown below:

In the Claims

In Column 30, Lines 66-67, Claim 9, delete "at least at least" and insert -- at least --, therefor.

Signed and Sealed this
Twenty-fifth Day of July, 2023

Katherine Kelly Vidal
*Director of the United States Patent and Trademark Office*